United States Patent
Abe et al.

(10) Patent No.: US 12,145,971 B2
(45) Date of Patent: Nov. 19, 2024

(54) POLYPEPTIDE SOLUTION, PRODUCTION METHOD FOR POLYPEPTIDE FIBER, AND ARTIFICIAL POLYPEPTIDE

(71) Applicants: Spiber Inc., Yamagata (JP); Kojima Industries Corporation, Aichi (JP)

(72) Inventors: Ayumi Abe, Tsuruoka (JP); Keisuke Morita, Tsuruoka (JP); Kenji Kurachi, Tsuruoka (JP); Yunosuke Abe, Tsuruoka (JP)

(73) Assignee: Spiber Inc., Yamagata (JP)

( * ) Notice: Subject to any disclaimer, the term of this patent is extended or adjusted under 35 U.S.C. 154(b) by 825 days.

(21) Appl. No.: 16/611,315

(22) PCT Filed: May 9, 2018

(86) PCT No.: PCT/JP2018/017953
§ 371 (c)(1),
(2) Date: Nov. 6, 2019

(87) PCT Pub. No.: WO2018/207827
PCT Pub. Date: Nov. 15, 2018

(65) Prior Publication Data
US 2020/0165311 A1     May 28, 2020

(30) Foreign Application Priority Data
May 10, 2017 (JP) ................ 2017-094017

(51) Int. Cl.
*C07K 14/47* (2006.01)
*D01D 5/06* (2006.01)
*D01F 4/00* (2006.01)

(52) U.S. Cl.
CPC ........... *C07K 14/4741* (2013.01); *D01D 5/06* (2013.01); *D01F 4/00* (2013.01); *C08L 2203/12* (2013.01)

(58) Field of Classification Search
CPC ........ C07K 14/4741; D01D 5/06; D01F 4/00; C08L 2203/12
USPC ....................................................... 530/423
See application file for complete search history.

(56) References Cited

U.S. PATENT DOCUMENTS

| | | | | |
|---|---|---|---|---|
| 9,644,012 B2 * | 5/2017 | Johansson | ............... | C12N 15/62 |
| 10,975,206 B2 * | 4/2021 | Ishida et al. | ............. | C08J 3/097 |
| | | | | 106/154.11 |
| 2013/0065278 A1 | 3/2013 | Johansson et al. | | |

FOREIGN PATENT DOCUMENTS

| | | | |
|---|---|---|---|
| JP | H05-170926 A | 7/1993 | |
| JP | 2009-144282 A | 7/2009 | |
| JP | 2010-081936 A | 4/2010 | |
| JP | 2010-236149 A | 10/2010 | |
| JP | 2011-207858 A | 10/2011 | |
| JP | 2016-160211 A | 9/2016 | |
| WO | 03/018673 A1 | 3/2003 | |
| WO | WO2006058673 A1 * | 6/2006 | ............... C08H 1/06 |
| WO | 2013/065650 A1 | 5/2013 | |
| WO | 2013/065651 A1 | 5/2013 | |
| WO | 2016/163337 A1 | 10/2016 | |
| WO | 2017/131196 A1 | 8/2017 | |

OTHER PUBLICATIONS

Jin et al: Small Ruminant Research: Keratin 26 a novel member of the goat type I Keratin gene family; vol. 93, pp. 24-30 (Year: 2010).*
International Search Report issued in corresponding International Patent Application No. PCT/JP2018/017953 dated Aug. 7, 2018.
International Preliminary Report on Patentability and Written Opinion issued in corresponding International Patent Application No. PCT/JP2018/017953 dated Nov. 21, 2019.
"Structure and Physical Properties of Wool, First Edition," Japan Wool Industry Association, 125-133 (2015) (see partial English translation).
Jin et al., "Keratin 26, a novel member of the goat type I keratin gene family," Small Ruminant Research, 93: 24-30 (2010).
KRT26-Keratin, type I cytoskeletal 26—*Bos taurus* (Bovine), http://www.uniprot.org/uniprot/A6H712 (2007).
Rogers et al., "The human type I keratin gene family: Characterization of new hair follicle specific members and evaluation of the chromosome 17q21.2 gene domain," Differentiation, 72: 527-540 (2004).
KRT26-Keratin, type I cytoskeletal 26—*Mus musculus* (Mouse), http://www.uniprot.org/uniprot/Q3TRJ4 (2005).
Hesse et al., "Comprehensive analysis of keratin gene clusters in humans and rodents," European Journal of Cell Biology, 83: 19-26 (2004).

\* cited by examiner

*Primary Examiner* — Tekchand Saidha
(74) *Attorney, Agent, or Firm* — Morgan, Lewis & Bockius LLP

(57) ABSTRACT

The present invention relates to a polypeptide solution in which a polypeptide including an amino acid sequence derived from type I keratin that belongs to Cluster Ia is dissolved in a solvent including a formic acid or a solvent including an aprotic polar agent having a dipole moment of 3.0 D or more and an inorganic salt.

14 Claims, 6 Drawing Sheets

Specification includes a Sequence Listing.

POLYPEPTIDE SOLUTION, PRODUCTION METHOD FOR POLYPEPTIDE FIBER, AND ARTIFICIAL POLYPEPTIDE

SEQUENCE LISTING SUBMISSION VIA EFS-WEB

A computer readable text file, entitled "SequenceListing.txt" created on or about May 16, 2023 with a file size of about 60,000 bytes contains the sequence listing for this application and is hereby incorporated by reference in its entirety.

TECHNICAL FIELD

The present invention relates to a polypeptide solution, a production method for a polypeptide fibre, and an artificial polypeptide.

BACKGROUND ART

In recent years, although there has been a tendency that the amount of animal hair supply is decreased, due to an increase in population in the wake of development of developing countries, a demand of animal hair increases every year, it becomes difficult to maintain balance between the demand and the supply. On the other hand, from a viewpoint of animal protection, there is a limit to cope with the difficulty by increasing the supply amount of natural animal hair.

Dissolving keratin which is a main constituent component of hair, reproducing thereof as a fibre, and reusing thereof has been attempted (Patent Literatures 1 and 2). More specifically, fine-powdered keratin is used in feeds or fertilizers, cosmetic bases, surfactants appropriate for the ecosystem, medical polymeric materials, and the like (Patent Literature 3). On the other hand, since natural animal hair has a complex structure (Patent Literature 1), no attempt has been made to produce fibres similar to artificial hair.

Keratin is classified into type I (acidic) keratin and type II (neutral or basic) keratin depending on an isoelectric point (Non-Patent Literature 1). The type I keratin can be classified into human I type epithelial keratin (K9-K28), human I type hair keratin (K31-K40), and non-human I type epithelial and hair keratin (K41-K70) (Non-Patent Literature 2). In addition, in Cluster I of the type I keratin, K26 (keratin 26) and K25 and K27 classified into Cluster Ia are known to have high bootstrap values, and to be close to an amino acid sequence. In particular, it is known that K26 has high sequence similarity regardless of the species (Non-Patent Literature 2).

CITATION LIST

Patent Literature

[Patent Literature 1] Japanese Unexamined Patent Publication No. 2010-236149
[Patent Literature 2] Japanese Unexamined Patent Publication No. 2016-160211
[Patent Literature 3] Japanese Unexamined Patent Publication No. H05-170926

Non Patent Literature

[Non-Patent Literature 1] Structure and Physical Properties of Wool, First edition, published by Japan Wool Industry Association, 2015, pp. 125-133
[Non-Patent Literature 2] Small Ruminat Research, Volume 93, 2010, pp. 24-30

SUMMARY OF INVENTION

Problems to be Solved by the Invention

As described above, a fibre replacing animal hair is sought. As described in Non-Patent Literature 2, due to gene analysis of keratin, the amino acid sequence has begun to be clear, but even the keratin has yet to be artificially produced.

An object of the present invention is to provide a polypeptide solution appropriate for producing polypeptide fibres including polypeptide derived from keratin. In addition, another object of the present invention is to provide a production method for polypeptide fibres using the polypeptide solution.

Means for Solving the Problems

As a result of intensive studies on a method of artificially producing keratin which is a main protein constituting natural hair and a method of producing fibres including keratin, the present inventors found that it is possible to artificially produce an artificial polypeptide fibre including the type I keratin, having the same stress, toughness, and elongation as those of natural hair, thereby completing the present invention.

That is, the present invention relates to the following inventions, for example.

[1] A polypeptide solution in which polypeptide including an amino acid sequence derived from type I keratin that belongs to Cluster Ia is dissolved in a solvent including a formic acid or a solvent including an aprotic polar agent having a dipole moment of 3.0 D or more and an inorganic salt.

[2] The polypeptide solution according to [1], wherein the solvent including an aprotic polar agent having a dipole moment of 3.0 D or more and an inorganic salt further includes a reducing agent.

[3] The polypeptide solution according to [2], wherein the reducing agent is at least one selected from the group consisting of thiols, tris(2-carboxyethyl)phosphine hydrochloride, tris(hydroxypropyl)phosphine, and sodium pyrosulfite.

[4] The polypeptide solution according to [3], wherein the thiols are at least one selected from the group consisting of dithiothreitol, β-mercaptoethanol, 3-mercapto-1,2-propandiol, 1,2-ethanthiol, thioglycolic acid, and ammonium thioglycolate (ATG).

[5] The polypeptide solution according to any one of [1] to [4], wherein the aprotic polar agent having a dipole moment of 3.0 D or more is at least one selected from the group consisting of dimethyl sulfoxide, N,N-dimethylformamide, N,N-dimethylacetamide, 1,3-dimethyl-2-imidazolidone, N-methyl-2-pyrrolidone, and acetonitrile.

[6] The polypeptide solution according to any one of [1] to [5], wherein the inorganic salt is at least one selected from the group consisting of alkaline metal halide, alkaline earth metal halide, alkaline earth metal nitrate, and thiocyanate.

[7] The polypeptide solution according to any one of [1] to [6], wherein the type I keratin that belongs to Cluster Ia is selected from the group consisting of keratin 25, keratin 26, and keratin 27.

[8] A production method for polypeptide fibre using the polypeptide solution according to any one of [1] to [7], the method comprising:

a step of using the polypeptide solution as a dope solution, extruding the dope solution from an orifice to a coagulation solution, and obtaining an undrawn yarn.

[9] The production method for polypeptide fibres according to [8], further comprising:
a step of drawing the undrawn yarn.

[10] The production method for polypeptide fibres according to [8] or [9], wherein the coagulation solution is at least one selected from the group consisting of methanol, ethanol, and 2-propanol.

[11] An expression vector having a nucleic acid sequence that encodes polypeptide having an amino acid sequence derived from the type I keratin that belongs to Cluster Ia and one or a plurality of regulatory sequences operably connected to the nucleic acid sequence.

[12] A host transformed with the expression vector according to [11].

[13] A method of producing artificial polypeptide, comprising:
culturing the host according to [12], proliferating the host, and inducing expression of the polypeptide.

[14] An artificial polypeptide comprising:
an amino acid sequence derived from type I keratin that belongs to Cluster Ia.

[15] The artificial polypeptide according to [14], wherein the type I keratin that belongs to Cluster Ia is selected from the group consisting of keratin 25, keratin 26, and keratin 27.

[16] The artificial polypeptide according to [14] or [15], comprising:
an amino acid sequence selected from the group consisting of amino acid sequences represented by SEQ ID NOs: 1 to 16.

[17] A product comprising:
the artificial polypeptide according to any one of [14] to [16],
wherein the product is selected from the group consisting of fibres, yarn, films, foaming bodies, granular bodies, nanofibrils, gel, and resins.

Effects of the Invention

According to the present invention, it is possible to provide a polypeptide solution appropriate for producing polypeptide fibres including polypeptide derived from keratin. In addition, according to the present invention, it is possible to provide a production method for polypeptide fibres using the polypeptide solution.

EMBODIMENTS FOR CARRYING OUT THE INVENTION

Hereinafter, embodiments to carry out the present invention will be described in detail. Here, the present invention is not limited to the following embodiments.

[Polypeptide Solution]

A polypeptide solution according to the present embodiment is obtained by dissolving polypeptide including an amino acid sequence derived from type I keratin that belongs to Cluster Ia in a solvent. The solvent may be a solvent including a formic acid or a solvent including an aprotic polar agent having a dipole moment of 3.0 D or more and an inorganic salt. In addition, in the present specification, the "artificial polypeptide" is a term for distinguish thereof from polypeptide derived from nature, and includes artificially prepared (for example, by genetic recombination method) polypeptide. In the meaning, the artificial polypeptide may be polypeptide having the same amino acid sequence as a natural amino acid sequence, or may be polypeptide having an amino acid sequence different from the natural amino acid sequence.

<Polypeptide Including Amino Acid Sequence Derived from Type I Keratin that Belongs Cluster Ia>

The polypeptide according to the present invention may include an amino acid sequence derived from the type I keratin that belongs to Cluster Ia (hereinafter, simply referred to as "polypeptide of present invention"). As described in Non-Patent Literature 2, Cluster Ia is a cluster of the type I keratin that belongs to goat (*Capra hircus*) keratin 25 (K25) and keratin 26 (K26), and sheep (*Ovis aries*) keratin 25 (K25) and keratin 27 (K27), when cluster analysis of an amino acid sequence of keratin by a neighbor-joining method is performed.

In the present specification, the "amino acid sequence derived from the type I keratin that belongs to Cluster Ia" includes an amino acid sequence of the natural type I keratin classified into Cluster Ia when cluster analysis by the neighbor-joining method is performed, and an amino acid sequence obtained by changing an amino acid sequence of the natural type I keratin. Here, "includes an amino acid sequence" includes a case of consisting of the amino acid sequence and a case of adding other amino acid sequences in addition to the amino acid sequence.

As a specific example of the (natural) type I keratin that belongs to Cluster Ia, keratin 25 (K25), keratin 26 (K26), and keratin 27 (K27) are exemplified, and K26 is preferable.

Figure 1:
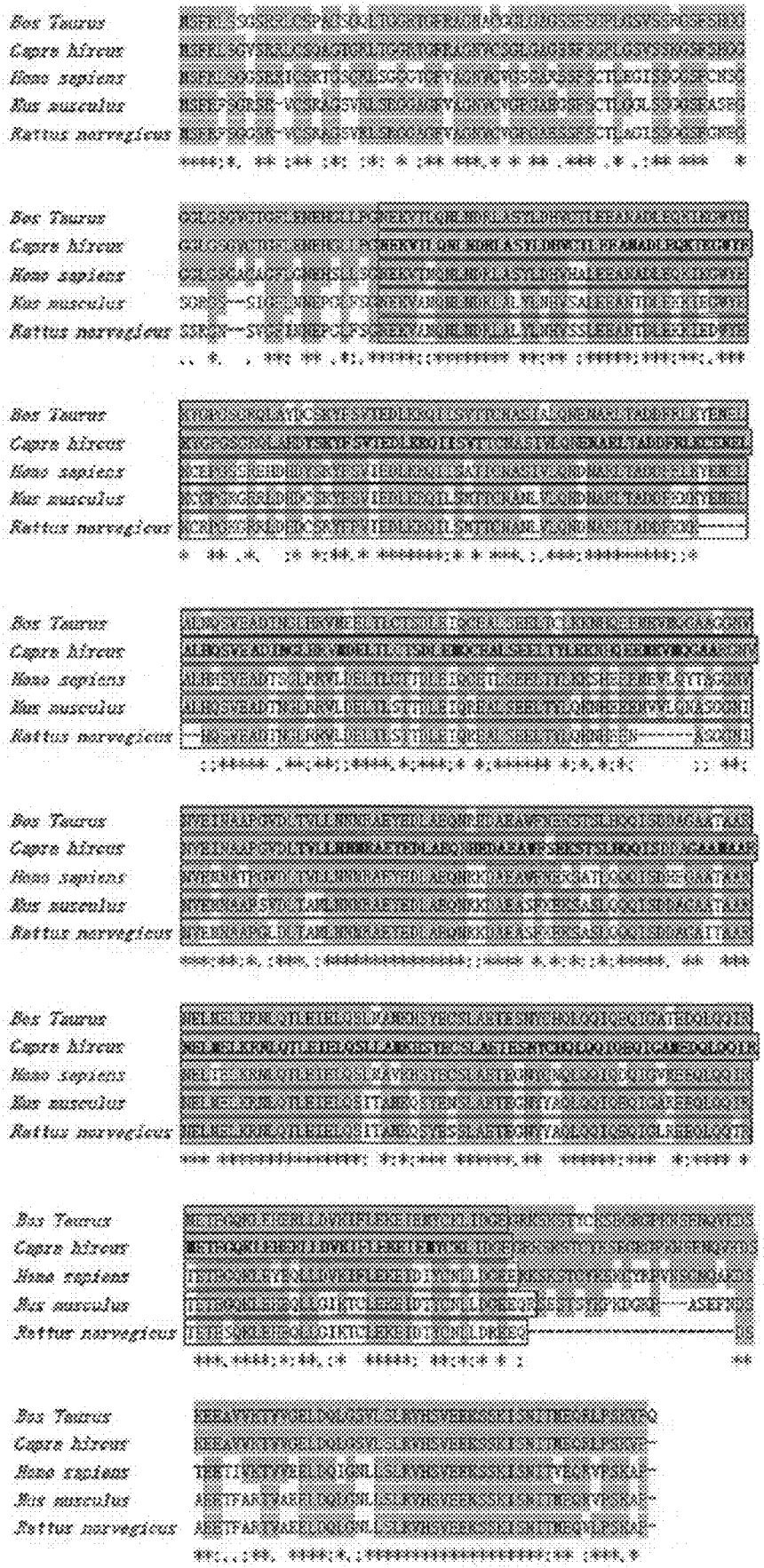
FIG. 1 is a diagram of alignment in which amino acid sequences of K26 derived from various organisms are compared. SEQ ID NO: 1 is *Capra hircus*, SEQ ID NO: 2 is *Bos taurus*, SEQ ID NO: 3 is *Homo sapiens*, SEQ ID NO: 4 is *Mus musculus* and SEQ ID NO: 5 is *Rattus norvegicus*.

FIG. 1 is a diagram of alignment in which amino acid sequences of K26 derived from various organisms are compared. As shown in Table 1, it is considered that K26 derived from goat (*Capra hircus*, NP_001272643.1), cow (*Bos taurus*, NM_001099096.1), human (*Homo sapiens*, BC132951.1), mouse (*Mus musculus*, BC116672.1), and rat (*Rattus norvegicus*, NM_001008823.1) has extremely high sequence identity (number of GenBank database in parentheses) and these proteins are conceivable to have extremely similar properties as protein. In FIG. 1, a shadowed residue shows a residue coincident with a goat K26 sequence. The asterisk under the alignment indicates sequence identity. The colon indicates conservative substitution, and the dot indicates non-conservative substitution.

The polypeptide of the present invention may be a polypeptide including an amino acid sequence obtained by performing modification corresponding to performing substitution, deletion, insertion and/or addition on one or a plurality of amino acid residues, on the amino acid sequence of the (natural) type I keratin that belongs to Cluster Ia as long as the polypeptide has properties as keratin (hereinafter, "referred to as modified polypeptide"). Specific examples of the modified polypeptide can include a modified polypeptide including an amino acid sequence represented by SEQ ID NO: 1, SEQ ID NO: 2, SEQ ID NO: 3, SEQ ID NO: 4, and SEQ ID NO: 5, an amino acid sequence having 85% or more sequence identity, preferably 90% or more sequence identity, more preferably 95% or more sequence identity, further more preferably 98% or more sequence identity, and even more preferably 99% or more sequence identity with the amino acid sequences thereof, and the like.

The modified polypeptide according to the present embodiment may include a tag sequence in one or both of N-terminal and C-terminal. By including the tag sequence, separation, fixation, detection, visualization, and the like of the polypeptide are possible.

Examples of the tag sequence can include an affinity tag using specific affinity (bindability, affinity) with other molecules. Specific examples of the affinity tag can include a histidine tag (His tag). Since the His tag is a short peptide in which about 4 to 10 histidine residues are arranged, and has properties of specifically binding to a metal ion such as nickel, the His tag can be used in separation of polypeptide by chelating metal chromatography. Specific examples of the tag sequence include an amino acid sequence (amino acid sequence including His tag) represented by SEQ ID NO: 17.

In addition, as the tag sequence, it is possible to use glutathione-S-transferase (GST) specifically binding to glutathione, maltose-binding protein (MBP) specifically binding to maltose, and the like.

In addition, as the tag sequence, it is possible to use an "epitope tag" using antigen-antibody reaction. By adding peptide (epitope) showing antigenicity as a tag sequence, it is possible to bind an antibody to the epitope. Examples of the epitope tag include a HA (peptide sequence of hemagglutinin of influenza virus), an myc tag, a FLAG tag, and the like. By using the epitope tag, it is possible to easily purify polypeptide with high specificity.

In addition, it is also possible to use those in which a tag sequence can be separated from specific protease. By performing protease treatment of protein adsorbed via the tag sequence, it is possible to recover polypeptide from which a tag sequence has been separated. Examples of a modified polypeptide including such a tag sequence can include an amino acid sequence represented by SEQ ID NO: 6, SEQ ID NO: 7, SEQ ID NO: 8, SEQ ID NO: 9, SEQ ID NO: 10, SEQ ID NO: 11, and SEQ ID NO: 12, an amino acid sequence having 85% or more sequence identity, preferably 90% or more sequence identity, more preferably 95% or more sequence identity, further more preferably 98% or more sequence identity, and even more preferably 99% or more sequence identity with the amino acid sequences thereof, and the like.

In addition, as polypeptide of the present invention, it is also possible to use modified polypeptide fused with a spider protein having high toughness and modified polypeptide having an amino acid sequence, in which poly A sequence which is one of properties of the spider protein is inserted, in order to increase intensity of polypeptide fibres. Specific examples of the modified polypeptide can include an amino acid sequence represented by SEQ ID NO: 13, SEQ ID NO: 14, SEQ ID NO: 15, and SEQ ID NO: 16, an amino acid sequence having 85% or more sequence identity, preferably 90% or more sequence identity, more preferably 95% or more sequence identity, further more preferably 98% or more sequence identity, and even more preferably 99% or more sequence identity with the amino acid sequences thereof, and the like.

<Method of Producing Artificial Polypeptide>

It is possible to produce the artificial polypeptide according to the present embodiment by culturing a host transformed with an expression vector having a nucleic acid sequence encoding polypeptide of the present invention and one or a plurality of regulatory sequences operably connected to the nucleic acid sequence, proliferating the host, and inducing expression of the polypeptide, for example.

(Nucleic Acid)

The method of producing a nucleic acid encoding polypeptide of the present invention is not particularly limited. For example, it is possible to produce the nucleic acid by a method of performing amplification by polymerase chain reaction (PCR) and the like, performing cloning, and performing modification by a gene engineering technique depending on the necessity, or a method of performing chemical synthesis, using a gene encoding natural keratin. In addition, the method of performing chemical synthesis of a nucleic acid is not particularly limited, and it is possible to perform chemical synthesis on a gene encoding polypeptide of the present invention by a method of connecting oligonucleotide automatically synthesized with a device such as AKTA oligopilot plus 10/100 (manufactured by GE Healthcare Japan Corporation) by a known gene engineering technique such as PCR, using information on amino acid sequence of keratin acquired from web database of NCBI.

(Regulatory Sequence)

A regulatory sequence is a sequence that controls expression of polypeptide in a host (for example, promoter, enhancer, ribosome-binding sequence, transcriptional termination sequence, and the like), and can be appropriately selected depending on the kind of the host. As a promoter, an inducible promoter that functions in a host cell and can induce expression of polypeptide may be used. In addition, the inducible promoter is a promoter that can control transcription by the presence of an inducer (expression inducing agent), the absence of a repressor, or physical causes such as increase or decrease in temperature, osmotic pressure, or pH values.

(Expression Vector and Host)

The kind of expression vectors can be appropriately selected depending on the kind of the host, such as a plasmid vector, a virus vector, a cosmid vector, a fosmid vector, and an artificial chromosome vector. As the expression vector, an expression vector, which is capable of self-replication in a host cell or capable of incorporating into a host chromosome, containing a promoter at a position capable of transcribing a nucleic acid encoding polypeptide is appropriately used.

Any of prokaryotic organisms and eukaryotic organisms such as yeast, filamentous fungus, insect cells, animal cells, and plant cells may be appropriately used as the host.

Preferable examples of the host of the prokaryotic organisms may include fungi that belong to genus *Escherichia*, genus *Brevibacillus*, genus *Serratia*, genus *Bacillus*, genus *Microbacterium*, genus *Brevibacterium*, genus *Corynebacterium*, and genus *Pseudomonas*. Examples of microorganisms that belong to genus *Escherichia* can include genus *Escherichia coli*. Examples of microorganisms that belong to genus *Brevibacillus* can include *Brevibacillus agri*. Examples of microorganisms that belong to genus *Serratia* can include *Serratia liquefaciens*. Examples of microorganisms that belong to genus *Bacillus* can include *Bacillus subtilis*. Examples of microorganisms that belong to genus *Microbacterium* can include *Bacillus subtilis*. Examples of microorganisms that belong to genus *Brevibacterium* may include *Brevibacterium divaricatum*. Examples of microorganisms that belong to genus *Corynebacterium* may include *Corynebacterium ammoniagenes*. Examples of microorganisms that belong to genus *Pseudomonas* may include *Pseudomonas putida*.

In a case where a prokaryotic organism is used as a host, examples of the expression vector introducing a nucleic acid encoding polypeptide of the present invention may include pBTrp2 (Beringerman Heim Co., Ltd.), pGEX (Pharmacia Limited), pUC18, pBluescriptII, pSupex, pET22b, pCold, pUB110, pNCO2 (Japanese Unexamined Patent Publication No. 2002-23 8569), and the like.

Examples of the host of the eukaryotic organisms may include yeast, filamentous fungus (mold), and the like. Examples of the yeast may include yeast that belongs to genus *Saccharomyces*, genus *Pichia*, genus *Schizosaccharomyces*, and the like. Examples of the filamentous fungus may include genus *Aspergillus*, genus *Penicillium*, genus *Trichoderma*, and the like.

In a case where a eukaryotic organism is used as a host, examples of the expression vector introducing a nucleic acid encoding polypeptide of the present invention may include YEP13 (ATCC3 7115), YEp24 (ATCC37051), and the like. As the method of introducing the expression vector to host cell, any method may be used as long as the method is a method of introducing DNA to the host cell. For example, examples of the method may include a method of using a calcium ion [Proc. Natl. Acad. Sci. USA, 69, 2110 (1972)], an electroporation method, a spheroplast method, a protoplast method, a lithium acetate method, a competent method, and the like.

(Production of Artificial Polypeptide)

As a method of expressing polypeptide of the present invention by a host transformed with an expression vector, it is possible to perform secretory production and fusion protein expression, and the like based on the method described in the molecular cloning second edition (Cold Spring Harbor Laboratory, 1989) in addition to direct expression.

In addition, it is possible to collect the artificial polypeptide according to the present embodiment by culturing a host transformed with an expression vector in a culture medium, generating and accumulating the artificial polypeptide in the culture medium, and separating and purifying thereof from the culture medium. The method of culturing a host in a culture medium may be performed by a method generally used in culturing of a host.

In a case where the transformed host is a prokaryotic organism such as *E. coli* or a eukaryotic organism such as yeast, as the culture medium, either of a natural medium or a synthetic medium may be used as long as the culture medium is a culture medium which contains a carbon source assimilated by the host, a nitrogen source, inorganic salts, and the like, and efficiently performs the culturing.

As the carbon source, a carbon source assimilated by the transformed host may be used, and for example, it is possible to use glucose, fructose, sucrose, and molasses containing thereof, a carbohydrate such as starch and starch hydrolysate, an organic acid such as acetate and propionic acid, and alcohols such as ethanol and propanol. As the nitrogen source, for example, it is possible to use ammonium salts of inorganic acid or organic acid such as ammonia, ammonium chloride, ammonium sulfate, ammonium acetate, and ammonium phosphate, other nitrogen-containing compounds, peptone, meat extract, yeast extract, corn steep liquor, casein hydrolysate, soybean cake and soybean cake hydrolysate, various fermentation microbial cells, and digests thereof. As the inorganic salts, it is possible to use primary potassium phosphate, secondary potassium phosphate, magnesium phosphate, magnesium sulfate, sodium chloride, ferrous sulfate, manganese sulfate, copper sulfate, and calcium carbonate.

It is possible to perform culturing of the prokaryotic organism such as *E. coli* or the eukaryotic organism such as yeast under an aerobic condition such as shaking culture or deep ventilation stirring culturing, for example. A culturing temperature is 15° C. to 40° C., for example. A culturing time is generally 16 hours to 7 days. It is preferable to maintain a pH of a culture medium at 3.0 to 9.0 in culturing. Adjustment of the pH of the culture medium can be performed by using an inorganic acid, an organic acid, an alkaline solution, urea, calcium carbonate, ammonia, and the like.

In addition, in culturing, depending on the necessity, antibiotics such as ampicillin and tetracycline may be added to the culture medium. In addition, when a host transformed with an expression vector using an inducible promoter as a promoter is cultured, an inducer may be added to the culture medium depending on the necessity. For example, when a host transformed with an expression vector using a lac promoter is cultured, an isopropyl-β-D-thiogalactopyranoside and the like may be added to the culture medium. When a host transformed with an expression vector using a trp promoter is cultured, an indoleacrylic acid and the like may be added to the culture medium.

(Separation and Purification of Artificial Polypeptide)

Separation and purification of the artificial polypeptide according to the present embodiment can be performed by a generally used method. For example, in a case where the artificial polypeptide is secreted from the host cell, it is possible to recover the artificial polypeptide from a culture supernatant. That is, it is possible to obtain a culture supernatant by treating a culture product including the host cell by a technique such as centrifugal separation, to use a method generally used in separation and purification of a known polypeptide from the culture supernatant, for example, a solvent extraction method, a salting out method by sulfuric acid and the like, a desalination method, a precipitation method by an organic solvent, an anion exchange chromatography using a resin such as diethylaminoethyl (DEAE)-sepharose, DIAION HPA-75 (manufactured by Mitsubishi Chemical Co., Ltd.), S-Sepharose FF (manufactured by Pharmacia Limited), a hydrophobic chromatography method using a resin such as butyl sepharose and phenyl sepharose, a gel filtration method using a molecular sieve, an affinity chromatography method, a chromatofocusing method, an electrophoresis such as isoelectric electrophoresis independently or in combination, and to obtain a purified artificial polypeptide (hereinafter, referred to as "purified sample").

In addition, in a case where the artificial polypeptide is expressed in a host cell in a dissolved state, after finishing culturing, the host cell is recovered by centrifugal separation, after suspension in an aqueous buffer solution, the host cell is pulverized by an ultrasonic pulverizer, a French press, a manton gaulin homogenizer, a dyno mill, and the like, and cell-free extract is obtained. It is possible to obtain a purified sample by using the same separation and purification method from a supernatant obtained by further performing centrifugal separation on the cell-free extract.

In addition, in a case where the artificial polypeptide is expressed by forming a non-soluble body as granule in the host cell, after recovering a host cell as described above, by performing pulverization and performing centrifugal separation, granule of the artificial polypeptide is recovered as a precipitation fraction. Granule of the recovered artificial polypeptide can be solubilized with a protein denaturing agent (hereinafter, simply referred to as "denaturing agent").

The non-soluble body may be washed with a buffer solution such as 20 mM of tris hydrochloric acid buffer solution (pH 8.0), a base such as sodium hydroxide, a solution such as alkali metal salt and alkaline earth metal salt, and an oxo acid before solubilization.

Examples of the denaturing agent may include urea, thiourea, guanidinium chloride (guanidine hydrochloride), a surfactant, and the like. In a case where urea and thiourea are used, the concentration is preferably 6 to 9 M. In a case where guanidinium chloride is used, the concentration is preferably 4 to 8 M. In addition, examples of the surfactant can include SDS, and 1 to 2 g may be added with respect to 1 g of protein.

After performing dissolution treatment with a denaturing agent, it is possible to obtain a purified sample by the same separation and purification method. For example, after dissolving the granule in urea, in a case of a method of precipitating an artificial polypeptide with an organic solvent, recovering, and purifying thereof, it is possible to use one or more aqueous solutions selected from a trichloro acetate (TCA) solution, a guanidine hydrochloride solution, an aqueous solution of a protein denaturing agent such as perchloric acid solution, and an acid substance such as hydrochloric acid, sulfuric acid, acetic acid, and phosphoric acid, and an organic solvent such as acetone and ethanol can be exemplified. In addition, an organic solvent, in which the ethanol includes normal propyl alcohol and isopropyl alcohol, may be used.

In order to precipitate an artificial polypeptide, it is possible to add 1 to 6 times the amount of the organic solvent, and preferably 2 to 5 times the amount of the organic solvent, to the dissolution solution using urea.

In addition, it is possible to purify and extract the artificial polypeptide from wet microbial cells or dry microbial cells of E. coli expressing the artificial polypeptide according to the present embodiment, using an aprotic polar agent having a dipole moment of 3.0 D or more. In addition, it is possible to extract the artificial polypeptide from the wet microbial cells or dry microbial cells of E. coli expressing the artificial polypeptide according to the present embodiment, using a solvent including a formic acid.

Table 1 describes an aprotic polar agent having a dipole moment of 3.0 D or more based on a solvent handbook (Kodansha Scientifics, 2007).

TABLE 1

| Organic solvent | Dipole moment (D) |
| --- | --- |
| DMSO | 4.30 |
| DMI | 4.05 |
| NMP (cyclic) | 4.09 |
| DMF | 3.86 |
| DMA | 3.72 |
| Acetonitrile | 3.44 |

As shown in Table 1, examples of the aprotic polar agent having a dipole moment of 3.0 D or more can include dimethyl sulfoxide (DMSO), N,N-dimethyl formamide (DMF), N,N-dimethyl acetamide (DMA), 1,3-dimethyl-2-imidazolidone (DMI), N-methyl-2-pyrrolidone (NMP), acetonitrile, and the like.

In a case where the artificial polypeptide according to the present embodiment is expressed by forming a non-soluble body as granule in the host cell, the non-soluble body is generally hardly soluble in the aprotic polar agent. Accordingly, it is possible to remove unnecessary components derived from a host cell by performing treatment by the aprotic polar agent, and it is possible to improve purity of the granule.

In addition, in a case where the artificial polypeptide is already acquired as granule from the host cell by the method, it is possible to further improve purity of the granule by performing treatment with the aprotic polar agent.

In a case where purification of the granule (improvement of purity) of the artificial polypeptide according to the present embodiment is an object, specifically, the aprotic polar agent may be added to the granule acquired from the host cell to obtain 1% to 10% (host cell dry weight (wt)/aprotic polar agent (vol)).

In addition, by adding an inorganic salt to the aprotic polar agent at a degree at which the granule is not dissolved, it is possible to further efficiently dissolve unnecessary components derived from the host cell.

Examples of the inorganic salt may include an alkaline metal halide, an alkaline earth metal halide, alkaline earth metal nitrate, thiocyanate, perchlorate, and the like.

Examples of the alkaline metal halide may include potassium bromide, sodium bromide, lithium bromide, potassium chloride, sodium chloride, lithium chloride, sodium fluoride, potassium fluoride, cesium fluoride, potassium iodide, sodium iodide, lithium iodide, and the like.

Examples of the alkaline earth metal halide may include calcium chloride, magnesium chloride, magnesium bromide, calcium bromide, magnesium iodide, calcium iodide, and the like.

Examples of the alkaline earth metal nitrate may include calcium nitrate, magnesium nitrate, strontium nitrate, barium nitrate, and the like.

Examples of the thiocyanate may include sodium thiocyanate, ammonium thiocyanate (guanidium thiocyanate), and the like.

Examples of the perchlorate may include ammonium perchlorate, potassium perchlorate, calcium perchlorate, silver perchlorate, sodium perchlorate, magnesium perchlorate, and the like.

An addition amount (wt) of the inorganic salt may be determined to be an optimal amount depending on the aprotic polar agent to be used and is not particularly limited, but is preferably 0% to 3% (wt/vol) with respect to a total amount of the aprotic polar agent (vol), for example.

A treatment temperature for the granule purification may be determined depending on the concentration of the inorganic salt to be added, the kind of the targeted artificial polypeptide, and the like and is not particularly limited, but may be a temperature of 10° C. to 60° C., and is preferably a temperature of 10° C. to 50° C., for example.

In the granule purification of the artificial polypeptide according to the present embodiment, the treatment time is not necessarily particularly limited as long as the targeted artificial polypeptide is dissolved, but considering industrial production, may be 10 to 100 minutes, preferably 10 to 60 minutes, and more preferably 10 to 30 minutes.

On the other hand, it is possible to dissolve the granulated non-soluble artificial polypeptide by using the aprotic polar agent having a dipole moment of 3.0 D or more added by a solvent including a formic acid or an inorganic salt at a higher concentration, and it is possible to extract the non-soluble artificial polypeptide by a host cell. In addition, in a case where a cysteine residue is included in the artificial polypeptide, it is preferable to add a reducing agent to the agent.

In this case, examples of the aprotic polar agent having a dipole moment of 3.0 D or more may include an solvent used in the granule purification as an appropriate solvent.

Regarding the inorganic salt, an inorganic salt used in the granule purification may be exemplified as an appropriate inorganic salt. The exemplified inorganic salt may be used alone, or two or more kinds thereof may be used in combination.

An addition amount (wt) of the inorganic salt may be determined to be an optimal amount depending on the aprotic polar agent to be used and is not particularly limited, but is preferably 0.1% to 20% (wt/vol) with respect to a total amount (vol) of the aprotic polar agent, for example.

In addition, examples of the reducing agent may include thiols such as dithiothreitol (DTT), β-mercaptoethanol (BME), 3-mercapto-1,2-propandiol, 1,2-ethanthiol, thioglycolic acid (TGA), and ammonium thioglycolate (ATG), phosphine derivatives such as tris(2-carboxyethyl)phosphine hydrochloride (TCEP), and tris(hydroxypropyl)phosphine (THPP), sodium pyrosulfite (SM), and the like.

An addition amount (wt) of the reducing agent is not particularly limited, but is preferably 0.1% to 10% (wt/vol), and more preferably 1% to 5%, with respect to a total amount (vol) of the aprotic polar agent to be used, for example.

A proportion of the artificial polypeptide (host cell dry weight wt) with respect to the addition amount (vol) of the formic acid and the like or the aprotic polar agent may be 1% to 20% (wt/vol), preferably 4% to 16%, and more preferably 6% to 12%.

In addition, it is possible to efficiently dissolve and extract the artificial polypeptide by increasing the temperature. A temperature at a time of increasing the temperature and performing dissolution may be determined depending on the solvent to be added, but is generally 10° C. to 90° C., preferably 30° C. to 85° C., and more preferably 40° C. to 80° C.

The treatment time is not necessarily particularly limited as long as the artificial polypeptide can be sufficiently dissolved, but considering industrial productivity and the yield, the treatment time is generally 20 to 80 minutes, preferably 20 to 70 minutes, and more preferably 20 to 60 minutes.

As a method of removing a non-soluble fraction from the aprotic polar agent in which the artificial polypeptide is dissolved and recovering the artificial polypeptide, a general method, for example, centrifugal separation, filter filtration such as drum filter and press filter, may be used. The condition of the centrifugal separation is not particularly limited, and examples of the condition can include room temperature (20±+5° C.), 5 to 20 minutes at 8000×g to 15000×g, and the like. In a case of filter filtration, it is possible to more efficiently recover a solvent, in which the polypeptide according to the present embodiment is dissolved, by using a filtration aid such as celite and diatomaceous earth and a precoat agent in combination. Separation of impurities may be performed twice or more.

<Method of Preparing Polypeptide Solution>

A polypeptide solution according to the present embodiment can be prepared as follows. For example, it is possible to prepare the polypeptide solution by adding polypeptide of the present invention (for example, artificial polypeptide according to the present embodiment) to a solvent obtained by adding an inorganic salt to an aprotic polar agent having a dipole moment of 3.0 D or more. In addition, for example, it is possible to prepare the polypeptide solution by adding the polypeptide of the present invention to a solvent including a formic acid. In a case where a cysteine residue is included in the polypeptide of the present invention, it is preferable to further add a reducing agent to the solvent (in particular, solvent in which an inorganic salt is added to an aprotic polar agent).

In a case where the artificial polypeptide according to the present embodiment is separated and purified in a state of being dissolved in a solvent as described above, it is possible to use the dissolution solution as the polypeptide solution according to the present embodiment by preparing thereof as the above-described solution.

Examples of the aprotic polar agent having a dipole moment of 3.0 D or more may include an agent described in the separation and purification of the artificial polypeptide as an appropriate agent.

Examples of the inorganic salt may include the inorganic salt described in the separation and purification of the artificial polypeptide as an appropriate inorganic salt. The inorganic salt may be used alone, or two or more kinds thereof may be used in combination.

An addition amount (wt) of the inorganic salt with respect to a total amount of the solvent may be determined to be an optimal amount depending on the aprotic polar agent to be used, and is preferably 0.1% to 20% (wt/vol), more preferably 1% to 10% (wt/vol), and further more preferably 1% to 5% (wt/vol), with respect to the aprotic polar agent (vol), for example.

Examples of the reducing agent may include a reducing agent described in the separation and purification of the artificial polypeptide as an appropriate reducing agent.

As an addition amount (wt) of the reducing agent with respect to a total amount of the solvent is preferably 0.1% to 10% (wt/vol) and more preferably 1% to 5%1, with respect to the aprotic polar agent (vol).

The solvent including a formic acid may be made of only the formic acid, or may include other agents, the above-described inorganic salt and/or the reducing agent, in addition to the formic acid.

A proportion of polypeptide dry weight (wt) of the present invention with respect to the addition amount (vol) of the formic acid and the like or the aprotic polar agent may be 5% to 35% (wt/vol), preferably 10% to 30%, and more preferably 12% to 28%.

In addition, it is possible to efficiently dissolve the polypeptide of the present invention by increasing the temperature. A temperature at a time of increasing the temperature and performing dissolution may be determined depending on the solvent to be added, but may be 10° C. to 120° C., preferably 30° C. to 120° C., and more preferably 40° C. to 120° C.

A treatment time at a time of increasing the temperature (temperature increase time) is not necessarily particularly limited as long as the polypeptide of the present invention can be sufficiently dissolved, but considering industrial productivity and the yield, the treatment time is generally 3 to 80 minutes, preferably 5 to 70 minutes, and more preferably 5 to 60 minutes.

<Use of Polypeptide Solution>

The polypeptide solution according to the present embodiment can be used as a dope solution. The dope solution is useful for spinning, a cast film solution, and the like. The dope solution may contain inevitable components, for example, impurities which have not been removed by the purification of the artificial polypeptide.

Viscosity of the dope solution in spinning may be appropriately set depending on the spinning method, and may be 100 to 15,000 cP (centipoise), more preferably 1,000 to 15,000 cP, and furthermore preferably 1,000 to 10,000 cP at 35° C., for example. Adjustment of the viscosity of the polypeptide solution according to the present embodiment can be performed by adjusting the concentration and/or the temperature of the polypeptide of the present invention in the solution, for example. The viscosity of the polypeptide solution can be measured by using product name "Electromagnetic yarn viscometer" manufactured by Kyoto Electronics Manufacturing Co., Ltd., for example.

The spinning method is not particularly limited as long as the spinning method is a method capable of spinning the polypeptide of the present invention, and examples thereof can include dry spinning, melt spinning, wet spinning, dry-wet spinning, and the like. As a preferable spinning method, the wet spinning or the dry-wet spinning can be exemplified.

<Dry-Wet Spinning—Drawing>

(1) Dry-Wet Spinning

In the dry-wet spinning, it is possible to obtain an undrawn thread-like yarn by extruding the polypeptide solution (dope solution) according to the present embodiment from a spinneret (nozzle) to a coagulation solution (coagulation solution tank), and solidifying the polypeptide of the present invention in the coagulation solution. The coagulation solution may be any solution as long as the coagulation solution is a solution capable of desolventizing, and examples thereof may include a lower alcohol having 1 to 5 carbon atoms such as methanol, ethanol, and 2-propanol, acetone, and the like. The coagulation solution may be added with appropriate water.

A temperature of the coagulation solution is preferably 5° C. to 30° C.

By extruding the dope solution in the coagulation solution of a desolventizing tank from the spinneret (orifice), a fibre is formed from the polypeptide of the present invention to obtain an undrawn yarn. In a case of a syringe pump having a nozzle having a diameter of 0.1 to 0.6 mm, an extrusion rate is preferably 0.2 to 6.0 ml/hour per 1 hole. In addition, a preferable extrusion rate is 1.4 to 4.0 ml/hour per 1 hole.

A length of the coagulation solution tank may be any length as long as desolventizing is efficiently performed, and is 200 to 500 mm, for example. A drawing rate of the undrawn yarn may be 1 to 20 m/minute, and preferably 1 to 3 m/minute, for example. A retention time may be 0.01 to 3 minutes, and preferably 0.05 to 0.15 minutes, for example. In addition, the undrawn yarn may be drawn (pre-drawn) in the coagulation solution. In order to suppress evaporation of the lower alcohol, the coagulation solution may be maintained at a low temperature, and drawn in a state of an undrawn yarn. The coagulation solution tank may be provided in multiple stages, and drawing may be performed in each stage or a specific stage, depending on the necessity. A drawing rate of the undrawn yarn is preferably 1 to 3 m/minutes.

(2) Drawing

Examples of the drawing method can include wet heat drawing, dry heat drawing, solidification bath drawing, and the like.

The dry heat drawing can be performed by using an electric tubular furnace, a dry heat plate, and the like. The temperature may be 140° C. to 270° C., and preferably 160° C. to 230° C. In the dry heat drawing, it is possible to draw an undrawn yarn (or pre-drawn yarn) by 0.5 to 8 times, and to preferably draw thereof by 1 to 4 times, for example.

Each of the wet heat drawing and the dry heat drawing may be performed alone, and may be performed in multiple stages or in combination. That is, the wet heat drawing and the dry heat drawing can be performed in appropriate combination, for example, first stage drawing is performed by the wet heat drawing and second stage drawing is performed by the dry heat drawing, or the first stage drawing is performed by the wet heat drawing, the second stage drawing is performed by the wet heat drawing, and further a third stage drawing is performed by the dry heat drawing, and the like.

A final drawing ratio in the drawing step is 5 to 20 times, and is preferably 6 to 11 times, for example, with respect to an undrawn yarn (or pre-drawn yarn).

<Product>

The artificial polypeptide fibre (artificial keratin fibre) formed from the artificial polypeptide according to the present invention can be applied to woven fabric, knit fabric, set fabric, non-woven fabric, and the like, as a fibre (long fibre, short fibre, multifilament, or monofilament, and the like) or a yarn (spun yarn, twisted yarn, false twisted yarn, processed yarn, blended filament yarn, blended yarn, and the like). In addition, the artificial polypeptide fibre can be applied to high intensity use such as ropes, suture threads for operation, flexible fasteners for electronic parts, and physiological active materials for transplantation (for example, artificial ligament and aortic band). In addition, it is possible to produce the artificial polypeptide based on the method described in U.S. Pat. No. 5,427,322 and the like.

In addition, the artificial polypeptide according to the present invention can be also applied to films, foaming bodies, granular bodies (spheres or non-spheres), nanofibrils, gel (hydrogel and the like), resins, and the equivalents, and can be produced based on the methods described in Japanese Unexamined Patent Publication No. 2009-505668, U.S. Pat. Nos. 5,678,283, 4,638,735, and the like.

EXAMPLES

Hereinafter, the present invention will be specifically described based on examples. Here, the present invention is not limited to the examples.

[(1) Synthesis of Nucleic Acid Encoding Artificial Polypeptide and Construction of Expression Vector]

Each of nucleic acids encoding an artificial polypeptide having amino acid sequences represented by SEQ ID NOs: 6 to 16 was synthesized. Each of the synthesized nucleic acids was cloned into a cloning vector (pUC118). Then, each of the synthesized nucleic acids was recombined to protein expression vector pET-22b (+) to obtain an expression vector.

The artificial polypeptide (PRT798) having an amino acid sequence represented by SEQ ID NO: 6 has an amino acid sequence in which an amino acid sequence (tag sequence and hinge sequence) represented by SEQ ID NO: 17 is added to an N terminal of an amino acid sequence of *Capra hircus* (GenBank Accession Number: NP_001272643.1) represented by SEQ ID NO: 1.

The artificial polypeptide (PRT800) having an amino acid sequence represented by SEQ ID NO: 7 has an amino acid sequence obtained by substituting cysteine of PRT798 (SEQ ID NO: 6) with serine.

The artificial polypeptide (PRT801) having an amino acid sequence represented by SEQ ID NO: 8 has an amino acid sequence obtained by substituting cysteine of PRT798 (SEQ ID NO: 6) with threonine.

The artificial polypeptide (PRT835) having an amino acid sequence represented by SEQ ID NO: 9 has an amino acid sequence obtained by deleting isoleucine, and substituting leucine with alanine or glycine, with respect to amino acid sequences formed of amino acid residues of 1st to 292nd from an N terminal of PRT798 (SEQ ID NO: 6).

The artificial polypeptide (PRT836) having an amino acid sequence represented by SEQ ID NO: 10 has an amino acid sequence obtained by deleting isoleucine, and substituting leucine or valine with alanine or glycine, with respect to amino acid sequences formed of amino acid residues of 1st to 292nd from the N terminal of PRT798 (SEQ ID NO: 6).

The artificial polypeptide (PRT856) having an amino acid sequence represented by SEQ ID NO: 11 has an amino acid sequence repeating a region not containing a tag sequence and a hinge sequence (SEQ ID NO: 17) of an N terminal of PRT835 (SEQ ID NO: 9).

The artificial polypeptide (PRT854) having an amino acid sequence represented by SEQ ID NO: 12 has an amino acid sequence repeating a region not containing a tag sequence and a hinge sequence (SEQ ID NO: 17) of an N terminal of PRT836 (SEQ ID NO: 10).

The artificial polypeptide (PRT840) having an amino acid sequence represented by SEQ ID NO: 13 has an amino acid sequence obtained by substituting 3 amino acid residues and substituting an amino acid sequence formed of GAAAAAG with amino acid and inserting thereof, with respect to amino acid sequences formed of 1st to 246nd amino acid residues from the N terminal of PRT836 (SEQ ID NO: 10).

The artificial polypeptide (PRT855) having an amino acid sequence represented by SEQ ID NO: 14 has an amino acid sequence repeating a region not containing a tag sequence and a hinge sequence (SEQ ID NO: 17) of an N terminal of PRT840 (SEQ ID NO: 13).

The artificial polypeptide (PRT837) having an amino acid sequence represented by SEQ ID NO: 15 has an amino acid sequence in which an amino acid sequence obtained by substituting leucine with alanine or glycine is fused, with respect to a tag sequence and a hinge sequence (SEQ ID NO: 17) in an order from the N terminal, an amino acid sequence formed of 142 amino acid residues obtained by changing spider yarn protein (GenBank Accession No: P46804.1, GI: 1174415) of *Nephila clavipes*, and amino acid residues of 293rd to 427th from the N terminal of PRT798 (SEQ ID NO: 6).

The artificial polypeptide (PRT838) having amino acid sequence represented by SEQ ID NO: 16 has an amino acid sequence obtained by substituting alanine of PRT837 (SEQ ID NO: 15) with valine.

[(2) Expression of Artificial Polypeptide]

An *E. coli* BLR (DE3) strain was transformed with pET-22b (+) expression vector obtained in (1). The transformed *E. coli* strain was cultured for 15 hours in a 2 mL of LB medium including ampicillin. After that, the culture solution was added to a 100 mL of seed culture medium (Table 2) including ampicillin such that $OD_{600}$ became 0.005. Maintaining the culture temperature at 30° C., flask culture was performed until $OD_{600}$ reached 5 (approximately 15 hours) to obtain a seed culture solution.

TABLE 2

| Seed culture medium | |
| --- | --- |
| Reagent | Concentration (g/L) |
| Glucose | 5.0 |
| $KH_2PO_4$ | 4.0 |
| $K_2HPO_4$ | 9.3 |
| Yeast extract | 6.0 |
| Ampicillin | 0.1 |

Subsequently, the seed culture solution was added to a jar fermenter to which a 500 mL of production medium (Table 3) was added such that $OD_{600}$ became 0.05, and the present culture was performed. The present culture was performed while maintaining the culture temperature at 37° C., constantly controlling the pH of the medium at 6.9, and maintaining a dissolved oxygen concentration in the medium at 20% of dissolved oxygen saturation concentration.

TABLE 3

| Production medium | |
| --- | --- |
| Reagent | Concentration (g/L) |
| Glucose | 12.0 |
| $KH_2PO_4$ | 9.0 |
| $MgSO_4 \cdot 7H_2O$ | 2.4 |
| Yeast extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| Adekanol (Adeka, LG-295S) | 0.1 (mL/L) |

Immediately after glucose in the production medium was completely consumed, a feed solution (glucose 455 g/1 L, yeast extract 120 g/1 L) was added at a rate of 1 mL/minute. Subsequently, under the same condition as that before the addition of the feed solution, the present culture was continued for 20 hours.

After that, 1 M of isopropyl-β-thiogalactopyranoside (IPTG) was added to the culture solution such that the final concentration became 1 mM, and expression of a targeted polypeptide (artificial polypeptide having amino acid sequences represented by SEQ ID NOs: 6 to 16) was induced. At a point when 20 hours elapsed after the addition of IPTG, the culture solution was subjected to centrifugal separation to recover microbial cells. SDS-PAGE was performed by using microbial cells prepared from the culture solution before the addition of IPTG and the culture solution after the addition of IPTG and expression of an artificial polypeptide was checked by appearance of a band of a targeted polypeptide size dependent on the addition of IPTG.

Figure 2:
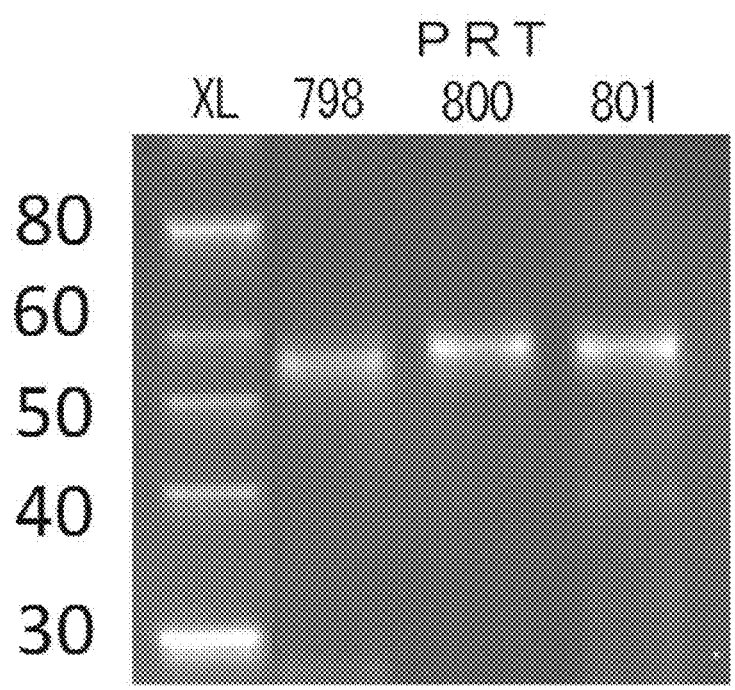
FIG. 2 is a photograph indicating a result of analyzing expression of artificial polypeptides of PRT798 (SEQ ID NO: 6), PRT800 (SEQ ID NO: 7), and PRT801 (SEQ ID NO: 8) by SDS-PAGE electrophoresis in the example.

FIG. 2 is a photograph showing a result in which expression of artificial polypeptides of PRT798 (SEQ ID NO: 6) (molecular weight 54 kDa), PRT800 (SEQ ID NO: 7) (molecular weight 54 kDa), and PRT801 (SEQ ID NO: 8)

(molecular weight 54 kDa) was analyzed by SDS-PAGE electrophoresis. As shown in Table 2, it was possible to detect expression at a position estimated by a theoretical molecular weight.

Figure 3:
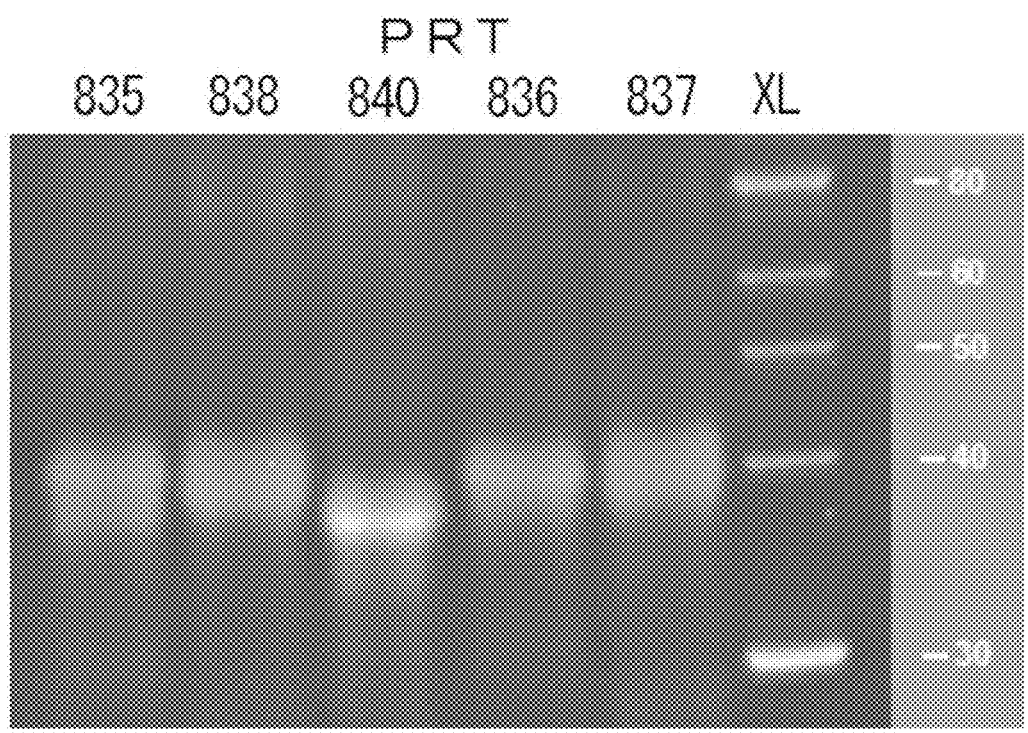
FIG. 3 is a photograph indicating a result of analyzing expression of artificial polypeptides of PRT835 (SEQ ID NO: 9), PRT838 (SEQ ID NO: 16), PRT840 (SEQ ID NO: 13), PRT836 (SEQ ID NO: 10), and PRT837 (SEQ ID NO: 15) by SDS-PAGE electrophoresis in the example.

Similarly, FIG. 3 is a photograph showing a result in which expression of artificial polypeptides of PRT835 (SEQ ID NO: 9) (molecular weight 30 kDa), PRT838 (SEQ ID NO: 16) (molecular weight 29 kDa), PRT840 (SEQ ID NO: 13) (molecular weight 27 kDa), PRT836 (SEQ ID NO: 10) (molecular weight 29 kDa), and PRT837 (SEQ ID NO: 15) (molecular weight 29 kDa) was analyzed by SDS-PAGE electrophoresis. As shown in Table 3, seemingly because of high hydrophobicity of the artificial polypeptides, a band was checked on a polymer side than the theoretical molecular weight.

Figure 4:
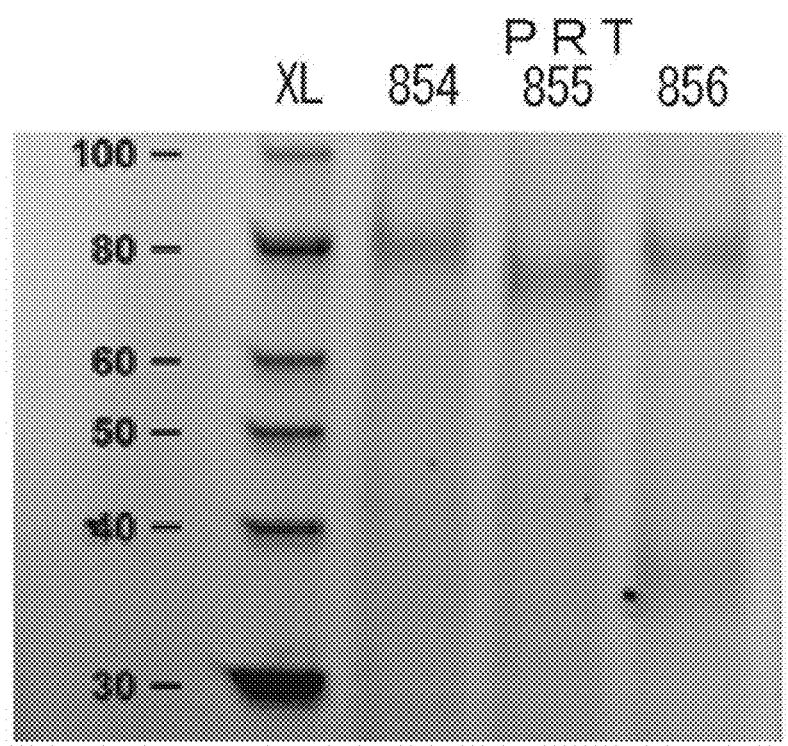
FIG. 4 is a photograph indicating a result of analyzing expression of artificial polypeptides of PRT854 (SEQ ID NO: 12), PRT855 (SEQ ID NO: 14), and PRT856 (SEQ ID NO: 11) by SDS-PAGE electrophoresis in the example.

In addition, FIG. 4 is a photograph showing a result in which expression of artificial polypeptides of PRT854 (SEQ ID NO: 12), PRT855 (SEQ ID NO: 14), and PRT856 (SEQ ID NO: 11) was analyzed by SDS-PAGE electrophoresis. As shown in Table 4, in the case of the artificial polypeptides as well, a band was checked on a polymer side than the theoretical molecular weight.

As the conclusion, it was also possible to efficiently express and produce any of the artificial polypeptides provided as described above.

[(3) Production of Artificial Polypeptide Fibre]

<Purification of Artificial Polypeptide>

E. coli BLR (DE3) expressing each of the 11 kinds of artificial polypeptides as non-soluble bodies was suspended in a solution in which a 20 mM of tris hydrochloric acid buffer solution (pH 8.0) was added to 100 mM of NaCl. 0.9 μg/g of DNase (manufactured by SIGMA-ALDRICH) (per 1 g of microbial cells) and 82 μg/g of Lysozyme (manufactured by Thermo Fisher Scientific) (per 1 g of microbial cells) were added to the suspension, and treated two times at room temperature and 600 bar of pressure by using a high pressure homogenizer (Panda plus) manufactured by GEA. NiroSoavi to pulverize microbial cells. After the pulverization, the microbial cell pulverization product was treated at 11,000×g for 20 hours using a centrifugal separator (freezing centrifugal separator Model 7000, manufactured by Kubota Corporation) to acquire a non-soluble body. In addition, the procedure was repeatedly performed to acquire a non-soluble body.

The obtained non-soluble body was washed with a 20 mM of Tris-HCL buffer solution (pH 7.4) to reach high purity. The washed non-soluble body was suspended in an 8 M of guanidine buffer solution (8 M guanidine hydrochloride, 10 mM sodium dihydrogen phosphate, 20 mM NaCl, 1 mM Tris-HCl, pH 7.0) to reach a concentration of 100 mg/mL, stirred at 60° C. for 30 minutes using a stirrer, and dissolved. After the dissolution, using a dialysis tube (cellulose tube 36/32 manufactured by Sanko Chemical Co., Ltd.), dialysis of the suspension was performed with water. After the dialysis, the obtained white cohesion polypeptide was recovered by centrifugal separation, moisture was removed therefrom by a freeze dryer, and freeze-dried powders of the artificial polypeptide was recovered.

A moisture content of the freeze-dried powders was measured by using a hybrid Karl Fischer moisture analyzer (MKH-700, manufactured by Kyoto Electronics Manufacturing Co., Ltd.).

<Preparation of Dope Solution>

4% of LiCl (wt/vol), 4% of DTT (wt/vol), and 15% of freeze-dried powders (wt/vol) of the artificial polypeptide prepared as described above were added to a DMSO solution, and stirred at 105° C. for 30 minutes, and the artificial polypeptide was completely dissolved to prepare a dope solution.

Viscosity of the dope solution was measured by using an electromagnetic yarn viscometer (manufactured by Kyoto Electronics Manufacturing Co., Ltd.). Viscosity of the dope solution of which measurement was performed in a sealed state at a rotation rate of 1000 rpm in a temperature range of 40° C. to 50° C. was 1000 to 1500 cP.

<Spinning>

The dope solution prepared as described above was filtered with a 3 μm of mesh metal filter, and then was charged in a syringe heated to 40° C., and through the flow of nitrogen gas, degassing was performed in a state of being maintained at 40° C. for 1 hour. After the degassing, the dope solution was discharged in a 100% methanol coagulation bath through a syringe with a nozzle hole having a diameter of 0.25 mm. At the time of discharging, a nozzle tip end of the syringe was installed to have a void between a surface of the coagulation solvent. The fibre obtained by coagulation was washed through two water baths, and dried through a dry heat plate. The obtained artificial polypeptide fibre (keratin type fibre) was wound using a winder. A total drawing ratio was 1.7 times.

<Measurement of Physical Properties of Artificial Polypeptide Fibre>

Physical properties of the artificial polypeptide fibre obtained as described above were measured by using an artificial polypeptide fibre of PRT798 (SEQ ID NO: 6).

Mechanical intensity of the artificial polypeptide fibre was measured by using FORCE TRANSDUCER 2519-101 of INSTRON (registered trademark) after the artificial polypeptide fibre was left still in a constant temperature-constant humidity tank of 20° C. and relative humidity of 65% (manufactured by Espec Corporation, LHL-113 type) for 24 hours. As a comparative example, natural wool was measured under the same condition.

Each of the diameters of the filaments was measured by using a microscope (manufactured by Nikon Corporation, ECLIPSE LV 100ND).

Figure 5:
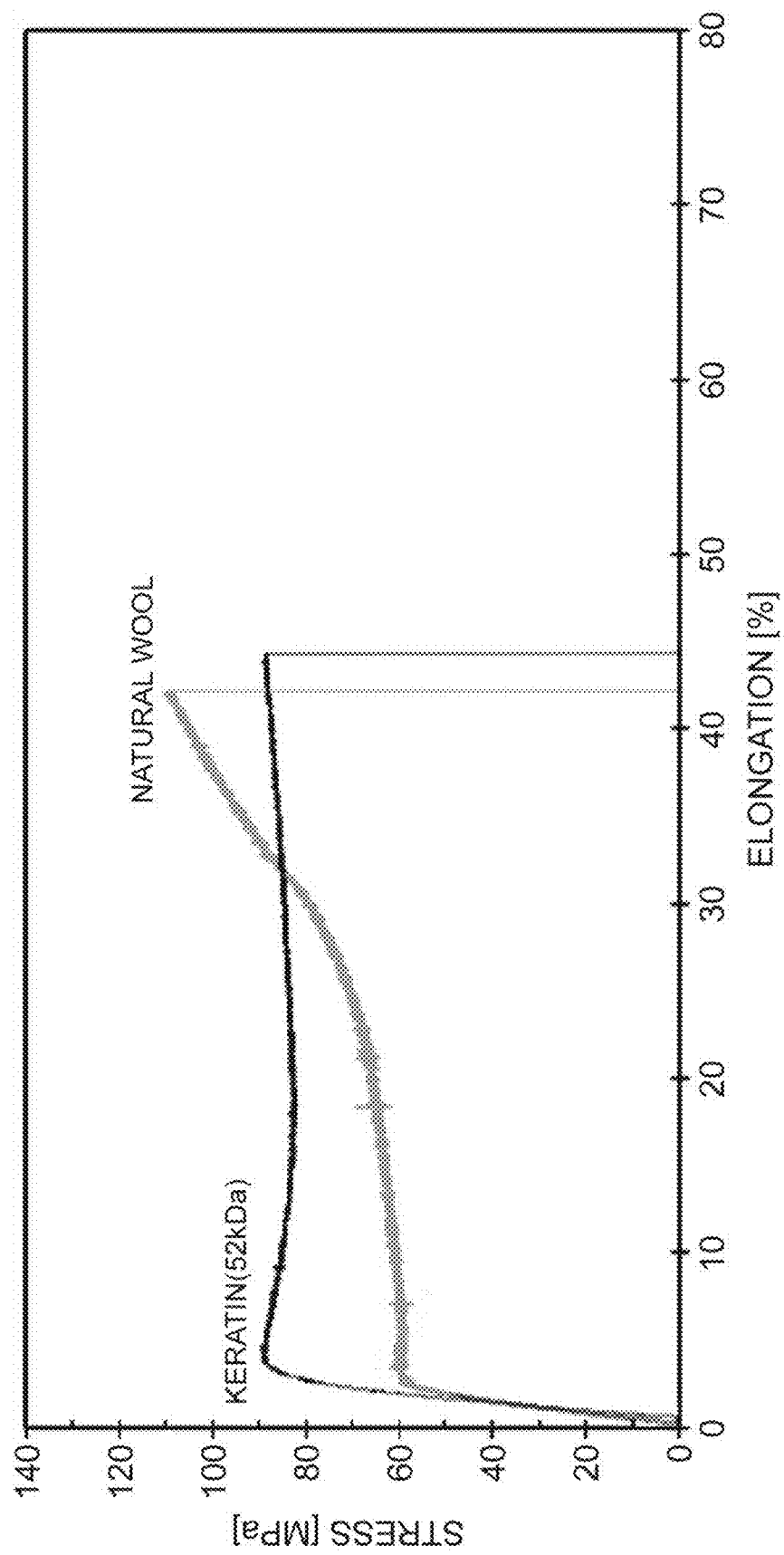
FIG. 5 is a photograph indicating a result of measuring mechanical intensity of an artificial polypeptide fibre (keratin type fibres) obtained from an artificial polypeptide of PRT798 (SEQ ID NO: 6) in the example.

The result is shown in Table 4 and FIG. 5. It was checked that the artificial polypeptide fibre (keratin type fibre) according to the present invention has an almost equivalent fibre diameter to that of natural wool having a complex structure, and also has almost the same mechanical features.

TABLE 4

| Sample | Diameter [μm] | Stress [MPa] | Toughness [MJ/m$^3$] | Elongation [%] |
| --- | --- | --- | --- | --- |
| Artificial polypeptide fibre (SEQ ID NO: 6) | 38.6 | 89.7 | 36.4 | 44.3 |
| Natural wool | 27.6 | 63.6 | 14.7 | 33.2 |

Figure 6:
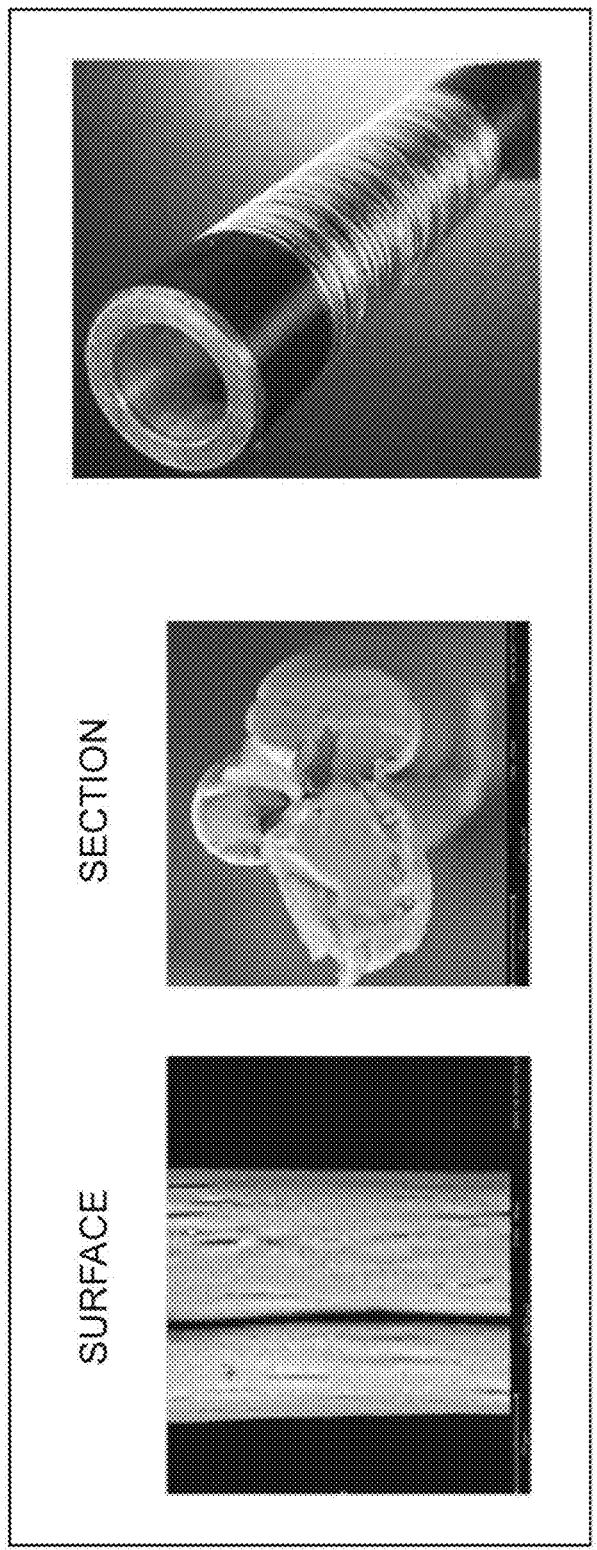
FIG. 6 is a photograph of scanning electron microscopy indicating a surface and a section of an artificial polypeptide fibre (keratin type fibres) obtained from an artificial polypeptide of PRT798 (SEQ ID NO: 6).

A surface and a section of the artificial polypeptide fibre obtained as described above were observed under a condition of an acceleration voltage of 15 kV using a scanning electron microscopy (PHENOM (trademark) 800-07334, Phenom-World). The result is shown in FIG. 6.

The invention claimed is:

1. A polypeptide solution in which an artificial polypeptide including the amino acid sequence selected from the group consisting of the amino acid sequences having 85% or more sequence identity with the amino acid sequences represented by SEQ ID NO: 1, SEQ ID NO: 2, SEQ ID NO: 3, SEQ ID NO: 4 and SEQ ID NO: 5 is dissolved in a solvent including a formic acid or a solvent including an aprotic polar agent having a dipole moment of 3.0 D or more and an inorganic salt, wherein the artificial polypeptide is expressed by a host transformed with an expression vector, and wherein the host is prokaryotic organism.

2. The polypeptide solution according to claim 1,
wherein the solvent including an aprotic polar agent having a dipole moment of 3.0 D or more and an inorganic salt further includes a reducing agent.

3. The polypeptide solution according to claim 2,
wherein the reducing agent is at least one selected from the group consisting of thiols, tris(2-carboxyethyl) phosphine hydrochloride, tris(hydroxypropyl)phosphine, and sodium pyrosulfite.

4. The polypeptide solution according to claim 3,
wherein the thiols are at least one selected from the group consisting of dithiothreitol, β-mercaptoethanol, 3-mercapto-1,2-propandiol, 1,2-ethanthiol, thioglycolic acid, and ammonium thioglycolate (ATG).

5. The polypeptide solution according to claim 1,
wherein the aprotic polar agent having a dipole moment of 3.0 D or more is at least one selected from the group consisting of dimethyl sulfoxide, N,N-dimethylforma mide, N,N-dimethylacetamide, 1,3-dimethyl-2-imidazolidone, N-methyl-2-pyrrolidone, and acetonitrile.

6. The polypeptide solution according to claim 1, wherein the inorganic salt is at least one selected from the group consisting of alkaline metal halide, alkaline earth metal halide, alkaline earth metal nitrate, sodium thiocyanate, and ammonium thiocyanate (guanidium thiocyanate).

7. A production method for polypeptide fiber using the polypeptide solution according to claim 1, the method comprising:

a step of using the polypeptide solution as a dope solution, extruding the dope solution from an orifice to a coagulation solution, and obtaining an undrawn yarn.

8. The production method for polypeptide fiber according to claim 7, further comprising:

a step of drawing the undrawn yarn.

9. The production method for polypeptide fiber according to claim 7, wherein the coagulation solution is at least one selected from the group consisting of methanol, ethanol, and 2-propanol.

10. The polypeptide solution according to claim 1, wherein the sequence identity is 90% or more.

11. The polypeptide solution according to claim 1, wherein the sequence identity is 95% or more.

12. The polypeptide solution according to claim 1, wherein the sequence identity is 98% or more.

13. The polypeptide solution according to claim 1, wherein the sequence identity is 99% or more.

14. The polypeptide solution according to claim 1, wherein the artificial polypeptide includes the amino acid sequence selected from the group consisting of the amino acid sequences represented by SEQ ID NO: 1, SEQ ID NO: 2, SEQ ID NO: 3, SEQ ID NO: 4 and SEQ ID NO: 5.

* * * * *

SEQUENCE LISTING

<160> NUMBER OF SEQ ID NOS: 17

<210> SEQ ID NO 1
<211> LENGTH: 468
<212> TYPE: PRT
<213> ORGANISM: Capra hircus

<400> SEQUENCE: 1

Met Ser Phe Arg Leu Ser Gly Val Ser Arg Arg Leu Cys Ser Gln Ala
1               5                   10                  15

Gly Thr Gly Arg Leu Thr Gly Gly Arg Thr Gly Phe Arg Ala Gly Asn
            20                  25                  30

Val Cys Ser Gly Leu Gly Ala Gly Ser Ser Phe Ser Gly Pro Leu Gly
        35                  40                  45

Ser Val Ser Ser Lys Gly Ser Phe Ser His Gly Gly Gly Leu Gly
    50                  55                  60

Ser Gly Val Cys Thr Gly Phe Leu Glu Asn Glu His Gly Leu Leu Pro
65                  70                  75                  80

Gly Asn Glu Lys Val Thr Leu Gln Asn Leu Asn Asp Arg Leu Ala Ser
                85                  90                  95

Tyr Leu Asp His Val Cys Thr Leu Glu Glu Ala Asn Ala Asp Leu Glu
                100                 105                 110

Gln Lys Ile Lys Gly Trp Tyr Glu Lys Tyr Gly Pro Gly Ser Gly Arg
            115                 120                 125

Gln Leu Ala His Asp Tyr Ser Lys Tyr Phe Ser Val Thr Glu Asp Leu
        130                 135                 140

Lys Arg Gln Ile Ile Ser Val Thr Thr Cys Asn Ala Ser Ile Val Leu
145                 150                 155                 160

Gln Asn Glu Asn Ala Arg Leu Thr Ala Asp Asp Phe Arg Leu Lys Cys
                165                 170                 175

Glu Asn Glu Leu Ala Leu His Gln Ser Val Glu Ala Asp Ile Asn Gly
                180                 185                 190

Leu His Arg Val Met Asp Glu Leu Thr Leu Cys Thr Ser Asp Leu Glu
            195                 200                 205

Met Gln Cys Glu Ala Leu Ser Glu Glu Leu Thr Tyr Leu Lys Lys Asn
        210                 215                 220

His Gln Glu Glu Met Lys Val Met Gln Gly Ala Ala Arg Gly Asn Val
225                 230                 235                 240

Asn Val Glu Ile Asn Ala Ala Pro Gly Val Asp Leu Thr Val Leu Leu
                245                 250                 255

Asn Asn Met Arg Ala Glu Tyr Glu Asp Leu Ala Glu Gln Asn His Glu
                260                 265                 270

Asp Ala Glu Ala Trp Phe Ser Glu Lys Ser Thr Ser Leu His Gln Gln
            275                 280                 285

Ile Ser Asp Asp Ala Gly Ala Ala Met Ala Ala Arg Asn Glu Leu Met
        290                 295                 300

Glu Leu Lys Arg Asn Leu Gln Thr Leu Glu Ile Glu Leu Gln Ser Leu
305                 310                 315                 320

Leu Ala Met Lys His Ser Tyr Glu Cys Ser Leu Ala Glu Thr Glu Ser
                325                 330                 335

Asn Tyr Cys His Gln Leu Gln Gln Ile Gln Gln Ile Gly Ala Met
                340                 345                 350

Glu Asp Gln Leu Gln Gln Ile Arg Met Glu Thr Glu Gly Gln Lys Leu
            355                 360                 365

-continued

Glu His Glu Arg Leu Leu Asp Val Lys Ile Phe Leu Glu Lys Glu Ile
    370                 375                 380

Glu Met Tyr Cys Lys Leu Ile Asp Gly Glu Gly Arg Lys Ser Lys Ser
385                 390                 395                 400

Thr Cys Tyr Lys Ser Glu Gly Arg Gly Pro Lys Asn Ser Glu Asn Gln
                405                 410                 415

Val Lys Asp Ser Lys Glu Glu Ala Val Val Lys Thr Val Val Gly Glu
                420                 425                 430

Leu Asp Gln Leu Gly Ser Val Leu Ser Leu Arg Val His Ser Val Glu
                435                 440                 445

Glu Lys Ser Ser Lys Ile Ser Asn Ile Thr Met Glu Gln Arg Leu Pro
450                 455                 460

Ser Lys Val Pro
465

<210> SEQ ID NO 2
<211> LENGTH: 469
<212> TYPE: PRT
<213> ORGANISM: Bos taurus

<400> SEQUENCE: 2

Met Ser Phe Arg Leu Ser Ser Gly Ser Arg Arg Leu Cys Ser Pro Ala
1               5                   10                  15

Gly Ser Gly Gln Leu Thr Gly Gly Arg Thr Gly Phe Arg Ala Gly Asn
                20                  25                  30

Ala Cys Gly Gly Leu Gly Ala Gly Ser Ser Phe Ser Gly Pro Leu Gly
            35                  40                  45

Ser Val Ser Ser Arg Gly Ser Phe Ser His Gly Gly Gly Leu Gly
    50                  55                  60

Ser Gly Val Cys Thr Gly Phe Leu Glu Asn Glu His Gly Leu Leu Pro
65                  70                  75                  80

Gly Asn Glu Lys Val Thr Leu Gln Asn Leu Asn Asp Arg Leu Ala Ser
                85                  90                  95

Tyr Leu Asp His Val Cys Thr Leu Glu Glu Ala Asn Ala Asp Leu Glu
                100                 105                 110

Gln Lys Ile Lys Gly Trp Tyr Glu Lys Tyr Gly Pro Gly Ser Gly Arg
            115                 120                 125

Gln Leu Ala Tyr Asp Cys Ser Lys Tyr Phe Ser Val Thr Glu Asp Leu
    130                 135                 140

Lys Arg Gln Ile Ile Ser Val Thr Thr Cys Asn Ala Ser Ile Ala Leu
145                 150                 155                 160

Gln Asn Glu Asn Ala Arg Leu Thr Ala Asp Asp Phe Arg Leu Lys Tyr
                165                 170                 175

Glu Asn Glu Leu Ala Leu Asn Gln Ser Val Glu Ala Asp Ile Asn Gly
                180                 185                 190

Leu His Arg Val Met Glu Glu Leu Thr Leu Cys Thr Ser Asp Leu Glu
            195                 200                 205

Ile Gln Cys Glu Ala Leu Ser Glu Glu Leu Thr Cys Leu Lys Lys Asn
    210                 215                 220

His Gln Glu Glu Met Lys Val Met Gln Gly Ala Ala Gly Gly Asn Val
225                 230                 235                 240

Asn Val Glu Ile Asn Ala Ala Pro Gly Val Asp Leu Thr Val Leu Leu
                245                 250                 255

Asn Asn Met Arg Ala Glu Tyr Glu Asp Leu Ala Glu Gln Asn Arg Glu
                260                 265                 270

```
Asp Ala Glu Ala Trp Phe Asn Glu Lys Ser Thr Ser Leu His Gln Gln
            275                 280                 285

Ile Ser Asp Asp Ala Gly Ala Ala Thr Ala Ala Arg Asn Glu Leu Met
        290                 295                 300

Glu Leu Lys Arg Asn Leu Gln Thr Leu Glu Ile Glu Leu Gln Ser Leu
305                 310                 315                 320

Met Ala Met Lys His Ser Tyr Glu Cys Ser Leu Ala Glu Thr Glu Ser
                325                 330                 335

Asn Tyr Cys His Gln Leu Gln Gln Ile Gln Glu Gln Ile Gly Ala Thr
            340                 345                 350

Glu Asp Gln Leu Gln Gln Ile Arg Met Glu Thr Glu Gly Gln Lys Leu
        355                 360                 365

Glu His Glu Arg Leu Leu Asp Val Lys Ile Phe Leu Glu Lys Glu Ile
370                 375                 380

Glu Met Tyr Cys Lys Leu Ile Asp Gly Glu Gly Arg Lys Ser Lys Ser
385                 390                 395                 400

Thr Tyr Cys Lys Ser Glu Gly Arg Gly Pro Lys Asn Ser Glu Asn Gln
                405                 410                 415

Val Lys Asp Ser Lys Glu Ala Val Val Lys Thr Val Val Gly Glu
            420                 425                 430

Leu Asp Gln Leu Gly Ser Val Leu Ser Leu Arg Val His Ser Val Glu
        435                 440                 445

Glu Lys Ser Ser Lys Ile Ser Asn Ile Thr Met Glu Gln Arg Leu Pro
450                 455                 460

Ser Lys Val Pro Gln
465

<210> SEQ ID NO 3
<211> LENGTH: 468
<212> TYPE: PRT
<213> ORGANISM: Homo sapiens

<400> SEQUENCE: 3

Met Ser Phe Arg Leu Ser Gly Gly Ser Arg Ile Cys Ser Arg Thr
1               5                   10                  15

Gly Ser Gly Arg Leu Ser Gly Gly Thr Gly Phe Val Ala Gly Asn
            20                  25                  30

Val Cys Val Gly Ser Gly Ala Arg Ser Ser Phe Ser Cys Thr Leu Glu
        35                  40                  45

Gly Ile Ser Ser Gly Gly Ser Phe Cys Asn Ser Gly Gly Gly Leu Gly
    50                  55                  60

Ser Gly Ala Cys Ala Gly Phe Leu Gly Asn Glu His Ser Leu Leu Ser
65                  70                  75                  80

Gly Asn Glu Lys Val Thr Met Gln Asn Leu Asn Asp Arg Leu Ala Ser
                85                  90                  95

Tyr Leu Asp His Val His Ala Leu Glu Glu Ala Asn Ala Asp Leu Glu
            100                 105                 110

Gln Lys Ile Lys Gly Trp Tyr Glu Lys Cys Glu Pro Gly Ser Ser Arg
        115                 120                 125

Glu His Asp His Asp Tyr Ser Arg Tyr Phe Ser Val Ile Glu Asp Leu
130                 135                 140

Lys Arg Gln Ile Ile Ser Ala Thr Ile Cys Asn Ala Ser Ile Val Leu
145                 150                 155                 160

Gln Asn Asp Asn Ala Arg Leu Thr Ala Asp Asp Phe Arg Leu Lys Tyr
```

```
                    165                 170                 175

Glu Asn Glu Leu Ala Leu His His Ser Val Glu Ala Asp Thr Ser Gly
            180                 185                 190

Leu Arg Arg Val Leu Asp Glu Leu Thr Leu Cys Thr Thr Asp Leu Glu
        195                 200                 205

Ile Gln Cys Glu Thr Leu Ser Glu Glu Leu Thr Tyr Leu Lys Lys Ser
    210                 215                 220

His Glu Glu Met Glu Val Leu Gln Tyr Thr Ala Gly Gly Asn Val
225                 230                 235                 240

Asn Val Glu Met Asn Ala Thr Pro Gly Val Asp Leu Thr Val Leu Leu
                245                 250                 255

Asn Asn Met Arg Ala Glu Tyr Glu Asp Leu Ala Glu Gln Asn Arg Lys
            260                 265                 270

Asp Ala Glu Ala Trp Phe Asn Glu Arg Ser Ala Thr Leu Gln Gln Gln
        275                 280                 285

Ile Ser Asp His Glu Gly Ala Ala Thr Ala Ala Arg Asn Glu Leu Thr
    290                 295                 300

Glu Leu Lys Arg Asn Leu Gln Thr Leu Glu Ile Glu Leu Gln Ser Leu
305                 310                 315                 320

Met Ala Val Lys His Ser Tyr Glu Cys Ser Leu Ala Glu Thr Glu Gly
                325                 330                 335

Asn Tyr Cys Asn Gln Leu Gln Gln Ile Gln Asp Gln Ile Gly Val Met
            340                 345                 350

Glu Glu Gln Leu Gln Gln Ile Arg Thr Glu Thr Glu Gly Gln Lys Leu
        355                 360                 365

Glu Tyr Glu Gln Leu Leu Asp Val Lys Ile Phe Leu Glu Lys Glu Ile
    370                 375                 380

Asp Ile Tyr Cys Asn Leu Leu Asp Gly Glu Arg Lys Ser Lys Ser
385                 390                 395                 400

Thr Cys Tyr Lys Ser Lys Gly Tyr Arg Pro Val Asn Ser Gly Asn Gln
                405                 410                 415

Ala Lys Asp Ser Thr Glu Glu Thr Ile Val Lys Thr Val Glu Glu
            420                 425                 430

Leu Asp Gln Ile Gly Asn Leu Leu Ser Leu Arg Val His Ser Val Glu
        435                 440                 445

Glu Lys Ser Ser Lys Ile Ser Asn Ile Thr Val Glu Gln Arg Val Pro
    450                 455                 460

Ser Lys Ala Pro
465

<210> SEQ ID NO 4
<211> LENGTH: 462
<212> TYPE: PRT
<213> ORGANISM: Mus musculus

<400> SEQUENCE: 4

Met Ser Phe Arg Phe Ser Gly Arg Ser Arg Val Cys Ser Arg Ala Gly
1               5                   10                  15

Ser Val Arg Leu Ser Arg Gly Gly Ala Gly Phe Val Ala Gly Asn Val
            20                  25                  30

Cys Val Gly Pro Gly Ala Glu Gly Ser Phe Ser Cys Thr Leu Gly Gly
        35                  40                  45

Leu Ser Ser Gly Gly Ser Phe Ala Ser Glu Gly Ser Gly Arg Gly Ser
    50                  55                  60
```

Ser Ile Gly Phe Leu Asn Asn Glu Pro Gly Leu Phe Ser Gly Asn Glu
 65                  70                  75                  80

Lys Val Ala Met Gln Asn Leu Asn Asp Arg Leu Ala Leu Tyr Leu Asn
                 85                  90                  95

His Val Ser Ala Leu Glu Glu Ala Asn Thr Asp Leu Glu Lys Lys Ile
            100                 105                 110

Glu Gly Trp Tyr Glu Lys Cys Gly Pro Gly Arg Gly Arg Arg Leu Asp
        115                 120                 125

His Asp Cys Ser Arg Tyr Phe Ser Val Ile Glu Asp Leu Lys Arg Gln
    130                 135                 140

Ile Leu Ser Met Thr Thr Cys Asn Ala Asn Leu Val Leu Gln Asn Asp
145                 150                 155                 160

Asn Ala Arg Leu Thr Ala Asp Asp Phe Lys Met Lys Tyr Glu Asn Glu
                165                 170                 175

Leu Ala Leu His Gln Ser Val Glu Ala Asp Thr Asn Gly Leu Arg Arg
            180                 185                 190

Val Leu Asp Glu Leu Thr Leu Ser Thr Thr Asp Leu Glu Ile Gln Arg
        195                 200                 205

Glu Ala Leu Ser Glu Glu Leu Thr Tyr Leu Gln Lys Asn His Glu Glu
    210                 215                 220

Glu Met Val Val Leu Gln Asn Ala Ser Gly Gly Asn Ile Asn Val Glu
225                 230                 235                 240

Met Asn Ala Ala Pro Ser Val Asp Leu Thr Ala Met Leu Asn Asn Met
                245                 250                 255

Arg Ala Glu Tyr Glu Asp Leu Ala Glu Gln Asn Arg Lys Asp Ala Glu
            260                 265                 270

Ala Ser Phe Lys Glu Lys Ser Ala Ser Leu Gln Gln Gln Ile Ser Asp
        275                 280                 285

Asp Ala Gly Ala Ala Thr Ala Ala Arg Asn Glu Leu Met Glu Leu Lys
    290                 295                 300

Arg Asn Leu Gln Thr Leu Glu Ile Glu Leu Gln Ser Ile Thr Ala Met
305                 310                 315                 320

Lys Gln Ser Tyr Glu Asn Ser Leu Ala Glu Thr Glu Gly Asn Tyr Tyr
                325                 330                 335

Ala Gln Leu Gln Gln Ile Gln Glu Gln Ile Gly Ala Arg Glu Glu Gln
            340                 345                 350

Leu Gln Gln Ile Arg Thr Glu Thr Glu Gly Gln Lys Leu Glu His Glu
        355                 360                 365

Gln Leu Leu Gly Ile Lys Thr Cys Leu Glu Lys Glu Ile Asp Thr Tyr
    370                 375                 380

Cys Asn Leu Leu Asp Gly Glu Glu Gln Arg Ser Glu Ser Thr Ser Tyr
385                 390                 395                 400

Lys Pro Lys Asp Gly Lys Pro Ala Ser Glu Phe Asn Asp Ser Ala Glu
                405                 410                 415

Glu Thr Phe Ala Arg Thr Val Ala Glu Glu Leu Asp Gln Leu Gly Asn
            420                 425                 430

Leu Leu Ser Leu Arg Val His Ser Val Glu Glu Lys Ser Ser Lys Ile
        435                 440                 445

Ser Asn Ile Thr Met Glu Gln Arg Val Pro Ser Lys Ala Pro
    450                 455                 460

<210> SEQ ID NO 5
<211> LENGTH: 430
<212> TYPE: PRT

<213> ORGANISM: Rattus norvegicus

<400> SEQUENCE: 5

```
Met Ser Phe Arg Phe Ser Gly Gly Ser Arg Val Cys Ser Arg Ala Gly
1               5                   10                  15

Ser Val Arg Leu Ser Arg Gly Gly Ala Gly Phe Val Ala Gly Asn Val
            20                  25                  30

Cys Val Gly Pro Gly Ala Glu Ser Ser Phe Ser Cys Thr Leu Ala Gly
        35                  40                  45

Ile Ser Ser Gly Gly Ser Phe Gly Asn Glu Gly Ser Ser Arg Gly Asn
    50                  55                  60

Ser Val Gly Phe Ile Asn Asn Glu Pro Gly Leu Phe Ser Gly Asn Glu
65                  70                  75                  80

Lys Val Ala Met Gln Asn Leu Asn Asp Arg Leu Ala Leu Tyr Leu Asn
                85                  90                  95

His Val Ser Ser Leu Glu Glu Ala Asn Thr Asp Leu Glu Lys Lys Ile
            100                 105                 110

Glu Asp Trp Tyr Glu Lys Cys Arg Pro Gly Lys Gly Arg Arg Leu Asp
        115                 120                 125

His Asp Cys Ser Arg Tyr Phe Pro Val Ile Glu Asp Leu Lys Arg Gln
    130                 135                 140

Ile Leu Ser Met Thr Thr Cys Asn Ala Asn Leu Val Leu Gln Asn Asp
145                 150                 155                 160

Asn Ala Arg Leu Thr Ala Asp Asp Phe Lys Met Lys His Gln Ser Val
                165                 170                 175

Glu Ala Asp Thr Asn Gly Leu Arg Arg Val Leu Asp Glu Leu Thr Leu
            180                 185                 190

Ser Thr Thr Asp Leu Glu Ile Gln Arg Glu Ala Leu Ser Glu Glu Leu
        195                 200                 205

Thr Tyr Leu Gln Lys Asn His Glu Glu Asn Ala Ser Gly Gly Asn Ile
    210                 215                 220

Asn Val Glu Met Asn Ala Ala Pro Gly Leu Asp Leu Thr Ala Met Leu
225                 230                 235                 240

Asn Asn Met Arg Ala Glu Tyr Glu Asp Leu Ala Glu Gln Asn Arg Lys
                245                 250                 255

Asp Ala Glu Ala Ser Phe Lys Glu Lys Ser Ala Ser Leu Gln Gln Gln
            260                 265                 270

Ile Ser Asp Asp Ala Gly Ala Ile Thr Ala Ala Arg Asn Glu Leu Met
        275                 280                 285

Glu Leu Lys Arg Asn Leu Gln Thr Leu Glu Ile Glu Leu Gln Ser Ile
    290                 295                 300

Thr Ala Met Lys Gln Ser Tyr Glu Ser Ser Leu Ala Glu Thr Glu Gly
305                 310                 315                 320

Asn Tyr Tyr Ala Gln Leu Gln Gln Ile Gln Glu Gln Ile Gly Leu Arg
                325                 330                 335

Glu Glu Gln Leu Gln Gln Thr Arg Thr Glu Thr Ser Gln Lys Leu
            340                 345                 350

Glu His Glu Gln Leu Leu Gly Ile Lys Thr Cys Leu Glu Lys Glu Ile
        355                 360                 365

Asp Thr Tyr Cys Asn Leu Leu Asp Arg Glu Glu Gln Asp Ser Ala Glu
    370                 375                 380

Glu Thr Phe Ala Arg Thr Val Ala Glu Glu Leu Asp Gln Leu Gly Asn
385                 390                 395                 400
```

-continued

```
Leu Leu Ser Leu Arg Val His Ser Val Glu Glu Lys Ser Ser Lys Ile
                405                 410                 415
Ser Asn Ile Thr Met Glu Gln Trp Leu Pro Ser Lys Ala Pro
            420                 425                 430

<210> SEQ ID NO 6
<211> LENGTH: 487
<212> TYPE: PRT
<213> ORGANISM: Artificial Sequence
<220> FEATURE:
<223> OTHER INFORMATION: PRT798

<400> SEQUENCE: 6

Met His His His His His His Ser Ser Gly Ser Ser Leu Glu Val Leu
1               5                   10                  15
Phe Gln Gly Pro Ser Phe Arg Leu Ser Gly Val Ser Arg Arg Leu Cys
            20                  25                  30
Ser Gln Ala Gly Thr Gly Arg Leu Thr Gly Gly Arg Thr Gly Phe Arg
        35                  40                  45
Ala Gly Asn Val Cys Ser Gly Leu Gly Ala Gly Ser Ser Phe Ser Gly
    50                  55                  60
Pro Leu Gly Ser Val Ser Ser Lys Gly Ser Phe Ser His Gly Gly Gly
65                  70                  75                  80
Gly Leu Gly Ser Gly Val Cys Thr Gly Phe Leu Glu Asn Glu His Gly
                85                  90                  95
Leu Leu Pro Gly Asn Glu Lys Val Thr Leu Gln Asn Leu Asn Asp Arg
            100                 105                 110
Leu Ala Ser Tyr Leu Asp His Val Cys Thr Leu Glu Glu Ala Asn Ala
        115                 120                 125
Asp Leu Glu Gln Lys Ile Lys Gly Trp Tyr Glu Lys Tyr Gly Pro Gly
    130                 135                 140
Ser Gly Arg Gln Leu Ala His Asp Tyr Ser Lys Tyr Phe Ser Val Thr
145                 150                 155                 160
Glu Asp Leu Lys Arg Gln Ile Ile Ser Val Thr Thr Cys Asn Ala Ser
                165                 170                 175
Ile Val Leu Gln Asn Glu Asn Ala Arg Leu Thr Ala Asp Asp Phe Arg
            180                 185                 190
Leu Lys Cys Glu Asn Glu Leu Ala Leu His Gln Ser Val Glu Ala Asp
        195                 200                 205
Ile Asn Gly Leu His Arg Val Met Asp Glu Leu Thr Leu Cys Thr Ser
    210                 215                 220
Asp Leu Glu Met Gln Cys Glu Ala Leu Ser Glu Leu Thr Tyr Leu
225                 230                 235                 240
Lys Lys Asn His Gln Glu Glu Met Lys Val Met Gln Gly Ala Ala Arg
                245                 250                 255
Gly Asn Val Asn Val Glu Ile Asn Ala Ala Pro Gly Val Asp Leu Thr
            260                 265                 270
Val Leu Leu Asn Asn Met Arg Ala Glu Tyr Glu Asp Leu Ala Glu Gln
        275                 280                 285
Asn His Glu Asp Ala Gly Ala Trp Phe Ser Lys Ser Thr Ser Leu
    290                 295                 300
His Gln Gln Ile Ser Asp Asp Ala Gly Ala Ala Met Ala Ala Arg Asn
305                 310                 315                 320
Glu Leu Met Glu Leu Lys Arg Asn Leu Gln Thr Leu Glu Ile Glu Leu
                325                 330                 335
```

```
Gln Ser Leu Leu Ala Met Lys His Ser Tyr Glu Cys Ser Leu Ala Glu
            340                 345                 350

Thr Glu Ser Asn Tyr Cys His Gln Leu Gln Gln Ile Gln Glu Gln Ile
            355                 360                 365

Gly Ala Met Glu Asp Gln Leu Gln Gln Ile Arg Met Glu Thr Glu Gly
        370                 375                 380

Gln Lys Leu Glu His Glu Arg Leu Leu Asp Val Lys Ile Phe Leu Glu
385                 390                 395                 400

Lys Glu Ile Glu Met Tyr Cys Lys Leu Ile Asp Gly Glu Gly Arg Lys
                405                 410                 415

Ser Lys Ser Thr Cys Tyr Lys Ser Glu Gly Arg Gly Pro Lys Asn Ser
            420                 425                 430

Glu Asn Gln Val Lys Asp Ser Lys Glu Glu Ala Val Val Lys Thr Val
            435                 440                 445

Val Gly Glu Leu Asp Gln Leu Gly Ser Val Leu Ser Leu Arg Val His
        450                 455                 460

Ser Val Glu Glu Lys Ser Ser Lys Ile Ser Asn Ile Thr Met Glu Gln
465                 470                 475                 480

Arg Leu Pro Ser Lys Val Pro
                485

<210> SEQ ID NO 7
<211> LENGTH: 487
<212> TYPE: PRT
<213> ORGANISM: Artificial Sequence
<220> FEATURE:
<223> OTHER INFORMATION: PRT800

<400> SEQUENCE: 7

Met His His His His His His Ser Ser Gly Ser Ser Leu Glu Val Leu
1               5                   10                  15

Phe Gln Gly Pro Ser Phe Arg Leu Ser Gly Val Ser Arg Arg Leu Ser
            20                  25                  30

Ser Gln Ala Gly Thr Gly Arg Leu Thr Gly Gly Arg Thr Gly Phe Arg
        35                  40                  45

Ala Gly Asn Val Ser Ser Gly Leu Gly Ala Gly Ser Ser Phe Ser Gly
    50                  55                  60

Pro Leu Gly Ser Val Ser Ser Lys Gly Ser Phe Ser His Gly Gly Gly
65                  70                  75                  80

Gly Leu Gly Ser Gly Val Ser Thr Gly Phe Leu Glu Asn Glu His Gly
                85                  90                  95

Leu Leu Pro Gly Asn Glu Lys Val Thr Leu Gln Asn Leu Asn Asp Arg
            100                 105                 110

Leu Ala Ser Tyr Leu Asp His Val Ser Thr Leu Glu Glu Ala Asn Ala
        115                 120                 125

Asp Leu Glu Gln Lys Ile Lys Gly Trp Tyr Glu Lys Tyr Gly Pro Gly
    130                 135                 140

Ser Gly Arg Gln Leu Ala His Asp Tyr Ser Lys Tyr Phe Ser Val Thr
145                 150                 155                 160

Glu Asp Leu Lys Arg Gln Ile Ile Ser Val Thr Thr Ser Asn Ala Ser
                165                 170                 175

Ile Val Leu Gln Asn Glu Asn Ala Arg Leu Thr Ala Asp Asp Phe Arg
            180                 185                 190

Leu Lys Ser Glu Asn Glu Leu Ala Leu His Gln Ser Val Glu Ala Asp
        195                 200                 205
```

Ile Asn Gly Leu His Arg Val Met Asp Glu Leu Thr Leu Ser Thr Ser
210                 215                 220

Asp Leu Glu Met Gln Ser Glu Ala Leu Ser Glu Leu Thr Tyr Leu
225                 230                 235                 240

Lys Lys Asn His Gln Glu Met Lys Val Met Gln Gly Ala Ala Arg
                245                 250                 255

Gly Asn Val Asn Val Glu Ile Asn Ala Ala Pro Gly Val Asp Leu Thr
                260                 265                 270

Val Leu Leu Asn Asn Met Arg Ala Glu Tyr Glu Asp Leu Ala Glu Gln
                275                 280                 285

Asn His Glu Asp Ala Glu Ala Trp Phe Ser Lys Ser Thr Ser Leu
290                 295                 300

His Gln Gln Ile Ser Asp Asp Ala Gly Ala Ala Met Ala Ala Arg Asn
305                 310                 315                 320

Glu Leu Met Glu Leu Lys Arg Asn Leu Gln Thr Leu Glu Ile Glu Leu
                325                 330                 335

Gln Ser Leu Leu Ala Met Lys His Ser Tyr Glu Ser Ser Leu Ala Glu
                340                 345                 350

Thr Glu Ser Asn Tyr Ser His Gln Leu Gln Gln Ile Gln Glu Gln Ile
                355                 360                 365

Gly Ala Met Glu Asp Gln Leu Gln Gln Ile Arg Met Glu Thr Glu Gly
370                 375                 380

Gln Lys Leu Glu His Glu Arg Leu Leu Asp Val Lys Ile Phe Leu Glu
385                 390                 395                 400

Lys Glu Ile Glu Met Tyr Ser Lys Leu Ile Asp Gly Glu Gly Arg Lys
                405                 410                 415

Ser Lys Ser Thr Ser Tyr Lys Ser Glu Gly Arg Gly Pro Lys Asn Ser
                420                 425                 430

Glu Asn Gln Val Lys Asp Ser Lys Glu Glu Ala Val Val Lys Thr Val
                435                 440                 445

Val Gly Glu Leu Asp Gln Leu Gly Ser Val Leu Ser Leu Arg Val His
                450                 455                 460

Ser Val Glu Glu Lys Ser Ser Lys Ile Ser Asn Ile Thr Met Glu Gln
465                 470                 475                 480

Arg Leu Pro Ser Lys Val Pro
                485

<210> SEQ ID NO 8
<211> LENGTH: 487
<212> TYPE: PRT
<213> ORGANISM: Artificial Sequence
<220> FEATURE:
<223> OTHER INFORMATION: PRT801

<400> SEQUENCE: 8

Met His His His His His Ser Ser Gly Ser Ser Leu Glu Val Leu
1               5                   10                  15

Phe Gln Gly Pro Ser Phe Arg Leu Ser Gly Val Ser Arg Arg Leu Thr
                20                  25                  30

Ser Gln Ala Gly Thr Gly Arg Leu Thr Gly Gly Arg Thr Gly Phe Arg
            35                  40                  45

Ala Gly Asn Val Thr Ser Gly Leu Gly Ala Gly Ser Ser Phe Ser Gly
        50                  55                  60

Pro Leu Gly Ser Val Ser Ser Lys Gly Ser Phe Ser His Gly Gly Gly
65                  70                  75                  80

```
Gly Leu Gly Ser Gly Val Thr Thr Gly Phe Leu Glu Asn Glu His Gly
                85                  90                  95
Leu Leu Pro Gly Asn Glu Lys Val Thr Leu Gln Asn Leu Asn Asp Arg
            100                 105                 110
Leu Ala Ser Tyr Leu Asp His Val Thr Thr Leu Glu Glu Ala Asn Ala
        115                 120                 125
Asp Leu Glu Gln Lys Ile Lys Gly Trp Tyr Glu Lys Tyr Gly Pro Gly
    130                 135                 140
Ser Gly Arg Gln Leu Ala His Asp Tyr Ser Lys Tyr Phe Ser Val Thr
145                 150                 155                 160
Glu Asp Leu Lys Arg Gln Ile Ile Ser Val Thr Thr Thr Asn Ala Ser
                165                 170                 175
Ile Val Leu Gln Asn Glu Asn Ala Arg Leu Thr Ala Asp Asp Phe Arg
            180                 185                 190
Leu Lys Thr Glu Asn Glu Leu Ala Leu His Gln Ser Val Glu Ala Asp
        195                 200                 205
Ile Asn Gly Leu His Arg Val Met Asp Glu Leu Thr Leu Thr Thr Ser
    210                 215                 220
Asp Leu Glu Met Gln Thr Glu Ala Leu Ser Glu Glu Leu Thr Tyr Leu
225                 230                 235                 240
Lys Lys Asn His Gln Glu Glu Met Lys Val Met Gln Gly Ala Ala Arg
                245                 250                 255
Gly Asn Val Asn Val Glu Ile Asn Ala Ala Pro Gly Val Asp Leu Thr
            260                 265                 270
Val Leu Leu Asn Asn Met Arg Ala Glu Tyr Glu Asp Leu Ala Glu Gln
        275                 280                 285
Asn His Glu Asp Ala Glu Ala Trp Phe Ser Glu Lys Ser Thr Ser Leu
    290                 295                 300
His Gln Gln Ile Ser Asp Asp Ala Gly Ala Ala Met Ala Ala Arg Asn
305                 310                 315                 320
Glu Leu Met Glu Leu Lys Arg Asn Leu Gln Thr Leu Glu Ile Glu Leu
                325                 330                 335
Gln Ser Leu Leu Ala Met Lys His Ser Tyr Glu Thr Ser Leu Ala Glu
            340                 345                 350
Thr Glu Ser Asn Tyr Thr His Gln Leu Gln Gln Ile Gln Glu Gln Ile
        355                 360                 365
Gly Ala Met Glu Asp Gln Leu Gln Gln Ile Arg Met Glu Thr Glu Gly
    370                 375                 380
Gln Lys Leu Glu His Glu Arg Leu Leu Asp Val Lys Ile Phe Leu Glu
385                 390                 395                 400
Lys Glu Ile Glu Met Tyr Thr Lys Leu Ile Asp Gly Glu Gly Arg Lys
                405                 410                 415
Ser Lys Ser Thr Thr Tyr Lys Ser Glu Gly Arg Gly Pro Lys Asn Ser
            420                 425                 430
Glu Asn Gln Val Lys Asp Ser Lys Glu Glu Ala Val Val Lys Thr Val
        435                 440                 445
Val Gly Glu Leu Asp Gln Leu Gly Ser Val Leu Ser Leu Arg Val His
    450                 455                 460
Ser Val Glu Glu Lys Ser Ser Lys Ile Ser Asn Ile Thr Met Glu Gln
465                 470                 475                 480
Arg Leu Pro Ser Lys Val Pro
                485
```

<210> SEQ ID NO 9
<211> LENGTH: 289
<212> TYPE: PRT
<213> ORGANISM: Artificial Sequence
<220> FEATURE:
<223> OTHER INFORMATION: PRT835

<400> SEQUENCE: 9

```
Met His His His His His His Ser Ser Gly Ser Ser Gly Glu Val Ala
1               5                   10                  15

Phe Gln Gly Pro Ser Phe Arg Gly Ser Gly Val Ser Arg Arg Ala Cys
            20                  25                  30

Ser Gln Ala Gly Thr Gly Arg Gly Thr Gly Gly Arg Thr Gly Phe Arg
        35                  40                  45

Ala Gly Asn Val Cys Ser Gly Ala Gly Ala Gly Ser Ser Phe Ser Gly
    50                  55                  60

Pro Gly Gly Ser Val Ser Ser Lys Gly Ser Phe Ser His Gly Gly Gly
65                  70                  75                  80

Gly Ala Gly Ser Gly Val Cys Thr Gly Phe Gly Glu Asn Glu His Gly
                85                  90                  95

Ala Ala Pro Gly Asn Glu Lys Val Thr Gly Gln Asn Ala Asn Asp Arg
            100                 105                 110

Gly Ala Ser Tyr Ala Asp His Val Cys Thr Gly Glu Glu Ala Asn Ala
        115                 120                 125

Asp Ala Glu Gln Lys Ile Lys Gly Trp Tyr Glu Lys Tyr Gly Pro Gly
    130                 135                 140

Ser Gly Arg Gln Gly Ala His Asp Tyr Ser Lys Tyr Phe Ser Val Thr
145                 150                 155                 160

Glu Asp Ala Lys Arg Gln Ser Val Thr Thr Cys Asn Ala Ser Val Gly
                165                 170                 175

Gln Asn Glu Asn Ala Arg Ala Thr Ala Asp Asp Phe Arg Gly Lys Cys
            180                 185                 190

Glu Asn Glu Ala Ala Gly His Gln Ser Val Glu Ala Asp Ile Asn Gly
        195                 200                 205

Ala His Arg Val Met Asp Glu Gly Thr Ala Cys Thr Ser Asp Gly Glu
    210                 215                 220

Met Gln Cys Glu Ala Ala Ser Glu Glu Gly Thr Tyr Ala Lys Lys Asn
225                 230                 235                 240

His Gln Glu Glu Met Lys Val Met Gln Gly Ala Ala Arg Gly Asn Val
                245                 250                 255

Asn Val Glu Ile Asn Ala Ala Pro Gly Val Asp Gly Thr Val Ala Gly
            260                 265                 270

Asn Asn Met Arg Ala Glu Tyr Glu Asp Ala Ala Glu Gln Asn His Glu
        275                 280                 285

Asp
```

<210> SEQ ID NO 10
<211> LENGTH: 289
<212> TYPE: PRT
<213> ORGANISM: Artificial Sequence
<220> FEATURE:
<223> OTHER INFORMATION: PRT836

<400> SEQUENCE: 10

```
Met His His His His His His Ser Ser Gly Ser Ser Gly Glu Gly Ala
1               5                   10                  15

Phe Gln Gly Pro Ser Phe Arg Gly Ser Gly Ala Ser Arg Arg Ala Cys
```

```
            20                  25                  30
Ser Gln Ala Gly Thr Gly Arg Gly Thr Gly Gly Arg Thr Gly Phe Arg
            35                  40                  45

Ala Gly Asn Gly Cys Ser Gly Ala Gly Ala Gly Ser Ser Phe Ser Gly
        50                  55                  60

Pro Gly Gly Ser Ala Ser Ser Lys Gly Ser Phe Ser His Gly Gly Gly
65                  70                  75                  80

Gly Ala Gly Ser Gly Gly Cys Thr Gly Phe Gly Glu Asn Glu His Gly
                85                  90                  95

Ala Ala Pro Gly Asn Glu Lys Ala Thr Gly Gln Asn Ala Asn Asp Arg
            100                 105                 110

Gly Ala Ser Tyr Ala Asp His Gly Cys Thr Gly Glu Glu Ala Asn Ala
        115                 120                 125

Asp Ala Glu Gln Lys Ile Lys Gly Trp Tyr Glu Lys Tyr Gly Pro Gly
130                 135                 140

Ser Gly Arg Gln Gly Ala His Asp Tyr Ser Lys Tyr Phe Ser Ala Thr
145                 150                 155                 160

Glu Asp Ala Lys Arg Gln Ser Gly Thr Thr Cys Asn Ala Ser Gly Gly
                165                 170                 175

Gln Asn Glu Asn Ala Arg Ala Thr Ala Asp Asp Phe Arg Gly Lys Cys
            180                 185                 190

Glu Asn Glu Ala Ala Gly His Gln Ser Ala Glu Ala Asp Ile Asn Gly
        195                 200                 205

Ala His Arg Gly Met Asp Glu Gly Thr Ala Cys Thr Ser Asp Gly Glu
210                 215                 220

Met Gln Cys Glu Ala Ala Ser Glu Glu Gly Thr Tyr Ala Lys Lys Asn
225                 230                 235                 240

His Gln Glu Glu Met Lys Ala Met Gln Gly Ala Ala Arg Gly Asn Gly
                245                 250                 255

Asn Ala Glu Ile Asn Ala Ala Pro Gly Gly Asp Gly Thr Ala Ala Gly
            260                 265                 270

Asn Asn Met Arg Ala Glu Tyr Glu Asp Ala Ala Glu Gln Asn His Glu
        275                 280                 285

Asp

<210> SEQ ID NO 11
<211> LENGTH: 558
<212> TYPE: PRT
<213> ORGANISM: Artificial Sequence
<220> FEATURE:
<223> OTHER INFORMATION: PR856

<400> SEQUENCE: 11

Met His His His His His Ser Ser Gly Ser Ser Gly Glu Val Ala
1               5                   10                  15

Phe Gln Gly Pro Ser Phe Arg Gly Ser Gly Val Ser Arg Arg Ala Cys
            20                  25                  30

Ser Gln Ala Gly Thr Gly Arg Gly Thr Gly Gly Arg Thr Gly Phe Arg
            35                  40                  45

Ala Gly Asn Val Cys Ser Gly Ala Gly Ala Gly Ser Ser Phe Ser Gly
        50                  55                  60

Pro Gly Gly Ser Val Ser Ser Lys Gly Ser Phe Ser His Gly Gly Gly
65                  70                  75                  80

Gly Ala Gly Ser Gly Val Cys Thr Gly Phe Gly Glu Asn Glu His Gly
                85                  90                  95
```

```
Ala Ala Pro Gly Asn Glu Lys Val Thr Gly Gln Asn Ala Asn Asp Arg
        100                 105                 110

Gly Ala Ser Tyr Ala Asp His Val Cys Thr Gly Glu Ala Asn Ala
        115                 120                 125

Asp Ala Glu Gln Lys Ile Lys Gly Trp Tyr Glu Lys Tyr Gly Pro Gly
        130                 135                 140

Ser Gly Arg Gln Gly Ala His Asp Tyr Ser Lys Tyr Phe Ser Val Thr
145                 150                 155                 160

Glu Asp Ala Lys Arg Gln Ser Val Thr Thr Cys Asn Ala Ser Val Gly
                165                 170                 175

Gln Asn Glu Asn Ala Arg Ala Thr Ala Asp Asp Phe Arg Gly Lys Cys
        180                 185                 190

Glu Asn Glu Ala Ala Gly His Gln Ser Val Glu Ala Asp Ile Asn Gly
        195                 200                 205

Ala His Arg Val Met Asp Glu Gly Thr Ala Cys Thr Ser Asp Gly Glu
        210                 215                 220

Met Gln Cys Glu Ala Ala Ser Glu Glu Gly Thr Tyr Ala Lys Lys Asn
225                 230                 235                 240

His Gln Glu Glu Met Lys Val Met Gln Gly Ala Ala Arg Gly Asn Val
                245                 250                 255

Asn Val Glu Ile Asn Ala Ala Pro Gly Val Asp Gly Thr Val Ala Gly
        260                 265                 270

Asn Asn Met Arg Ala Glu Tyr Glu Asp Ala Ala Glu Gln Asn His Glu
        275                 280                 285

Asp Ser Phe Arg Gly Ser Gly Val Ser Arg Arg Ala Cys Ser Gln Ala
        290                 295                 300

Gly Thr Gly Arg Gly Thr Gly Arg Gly Phe Arg Ala Gly Asn
305                 310                 315                 320

Val Cys Ser Gly Ala Gly Ala Gly Ser Ser Phe Ser Gly Pro Gly Gly
                325                 330                 335

Ser Val Ser Ser Lys Gly Ser Phe Ser His Gly Gly Gly Ala Gly
        340                 345                 350

Ser Gly Val Cys Thr Gly Phe Gly Glu Asn Glu His Gly Ala Ala Pro
        355                 360                 365

Gly Asn Glu Lys Val Thr Gly Gln Asn Ala Asn Asp Arg Gly Ala Ser
        370                 375                 380

Tyr Ala Asp His Val Cys Thr Gly Glu Glu Ala Asn Ala Asp Ala Glu
385                 390                 395                 400

Gln Lys Ile Lys Gly Trp Tyr Glu Lys Tyr Gly Pro Gly Ser Gly Arg
                405                 410                 415

Gln Gly Ala His Asp Tyr Ser Lys Tyr Phe Ser Val Thr Glu Asp Ala
        420                 425                 430

Lys Arg Gln Ser Val Thr Thr Cys Asn Ala Ser Val Gly Gln Asn Glu
        435                 440                 445

Asn Ala Arg Ala Thr Ala Asp Asp Phe Arg Gly Lys Cys Glu Asn Glu
        450                 455                 460

Ala Ala Gly His Gln Ser Val Glu Ala Asp Ile Asn Gly Ala His Arg
465                 470                 475                 480

Val Met Asp Glu Gly Thr Ala Cys Thr Ser Asp Gly Glu Met Gln Cys
                485                 490                 495

Glu Ala Ala Ser Glu Glu Gly Thr Tyr Ala Lys Lys Asn His Gln Glu
        500                 505                 510
```

```
Glu Met Lys Val Met Gln Gly Ala Ala Arg Gly Asn Val Asn Val Glu
            515                 520                 525
Ile Asn Ala Ala Pro Gly Val Asp Gly Thr Val Ala Gly Asn Asn Met
        530                 535                 540
Arg Ala Glu Tyr Glu Asp Ala Ala Glu Gln Asn His Glu Asp
545                 550                 555

<210> SEQ ID NO 12
<211> LENGTH: 558
<212> TYPE: PRT
<213> ORGANISM: Artificial Sequence
<220> FEATURE:
<223> OTHER INFORMATION: PRT854

<400> SEQUENCE: 12

Met His His His His His Ser Ser Gly Ser Gly Glu Gly Ala
1               5                   10                  15
Phe Gln Gly Pro Ser Phe Arg Gly Ser Gly Ala Ser Arg Arg Ala Cys
                20                  25                  30
Ser Gln Ala Gly Thr Gly Arg Gly Thr Gly Gly Arg Thr Gly Phe Arg
            35                  40                  45
Ala Gly Asn Gly Cys Ser Gly Ala Gly Ala Gly Ser Ser Phe Ser Gly
        50                  55                  60
Pro Gly Gly Ser Ala Ser Ser Lys Gly Ser Phe Ser His Gly Gly
65                  70                  75                  80
Gly Ala Gly Ser Gly Gly Cys Thr Gly Phe Gly Glu Asn Glu His Gly
                85                  90                  95
Ala Ala Pro Gly Asn Glu Lys Ala Thr Gly Gln Asn Ala Asn Asp Arg
            100                 105                 110
Gly Ala Ser Tyr Ala Asp His Gly Cys Thr Gly Glu Glu Ala Asn Ala
        115                 120                 125
Asp Ala Glu Gln Lys Ile Lys Gly Trp Tyr Glu Lys Tyr Gly Pro Gly
    130                 135                 140
Ser Gly Arg Gln Gly Ala His Asp Tyr Ser Lys Tyr Phe Ser Ala Thr
145                 150                 155                 160
Glu Asp Ala Lys Arg Gln Ser Gly Thr Thr Cys Asn Ala Ser Gly Gly
                165                 170                 175
Gln Asn Glu Asn Ala Arg Ala Thr Ala Asp Asp Phe Arg Gly Lys Cys
            180                 185                 190
Glu Asn Glu Ala Ala Gly His Gln Ser Ala Glu Ala Asp Ile Asn Gly
        195                 200                 205
Ala His Arg Gly Met Asp Glu Gly Thr Ala Cys Thr Ser Asp Gly Glu
    210                 215                 220
Met Gln Cys Glu Ala Ala Ser Glu Glu Gly Thr Tyr Ala Lys Lys Asn
225                 230                 235                 240
His Gln Glu Glu Met Lys Ala Met Gln Gly Ala Ala Arg Gly Asn Gly
                245                 250                 255
Asn Ala Glu Ile Asn Ala Ala Pro Gly Gly Asp Gly Thr Ala Ala Gly
            260                 265                 270
Asn Asn Met Arg Ala Glu Tyr Glu Asp Ala Ala Glu Gln Asn His Glu
        275                 280                 285
Asp Ser Phe Arg Gly Ser Gly Ala Ser Arg Arg Ala Cys Ser Gln Ala
    290                 295                 300
Gly Thr Gly Arg Gly Thr Gly Gly Arg Thr Gly Phe Arg Ala Gly Asn
305                 310                 315                 320
```

```
Gly Cys Ser Gly Ala Gly Ser Ser Phe Ser Gly Pro Gly Gly
            325                 330                 335

Ser Ala Ser Ser Lys Gly Ser Phe Ser His Gly Gly Gly Ala Gly
        340                 345                 350

Ser Gly Gly Cys Thr Gly Phe Gly Glu Asn Glu His Gly Ala Ala Pro
        355                 360                 365

Gly Asn Glu Lys Ala Thr Gly Gln Asn Ala Asn Asp Arg Gly Ala Ser
    370                 375                 380

Tyr Ala Asp His Gly Cys Thr Gly Glu Glu Ala Asn Ala Asp Ala Glu
385                 390                 395                 400

Gln Lys Ile Lys Gly Trp Tyr Glu Lys Tyr Gly Pro Gly Ser Gly Arg
                405                 410                 415

Gln Gly Ala His Asp Tyr Ser Lys Tyr Phe Ser Ala Thr Glu Asp Ala
            420                 425                 430

Lys Arg Gln Ser Gly Thr Thr Cys Asn Ala Ser Gly Gly Gln Asn Glu
        435                 440                 445

Asn Ala Arg Ala Thr Ala Asp Asp Phe Arg Gly Lys Cys Glu Asn Glu
    450                 455                 460

Ala Ala Gly His Gln Ser Ala Glu Ala Asp Ile Asn Gly Ala His Arg
465                 470                 475                 480

Gly Met Asp Glu Gly Thr Ala Cys Thr Ser Asp Gly Glu Met Gln Cys
                485                 490                 495

Glu Ala Ala Ser Glu Glu Gly Thr Tyr Ala Lys Lys Asn His Gln Glu
            500                 505                 510

Glu Met Lys Ala Met Gln Gly Ala Ala Arg Gly Asn Gly Asn Ala Glu
        515                 520                 525

Ile Asn Ala Ala Pro Gly Gly Asp Gly Thr Ala Ala Gly Asn Asn Met
    530                 535                 540

Arg Ala Glu Tyr Glu Asp Ala Ala Glu Gln Asn His Glu Asp
545                 550                 555

<210> SEQ ID NO 13
<211> LENGTH: 290
<212> TYPE: PRT
<213> ORGANISM: Artificial Sequence
<220> FEATURE:
<223> OTHER INFORMATION: PRT840

<400> SEQUENCE: 13

Met His His His His His Ser Ser Gly Ser Ser Glu Gly Ala
1               5                   10                  15

Phe Gln Gly Pro Ser Phe Arg Gly Ser Gly Ala Ser Arg Gly Ala Ala
                20                  25                  30

Ala Ala Ala Gly Ser Gln Ala Gly Thr Gly Arg Gly Thr Gly Gly Arg
            35                  40                  45

Thr Gly Phe Arg Ala Gly Asn Gly Cys Ser Gly Ala Gly Ala Ala
    50                  55                  60

Ala Ala Gly Ser Ser Phe Ser Gly Pro Gly Gly Ser Ala Ser Ser Lys
65                  70                  75                  80

Gly Ser Phe Ser His Gly Gly Ala Ala Ala Ala Gly Gly Ala Gly
                85                  90                  95

Ser Gly Gly Cys Thr Gly Phe Gly Glu Asn Glu His Gly Ala Ala Ala
            100                 105                 110

Ala Ala Gly Gly Asn Glu Lys Ala Thr Gly Gln Asn Ala Asn Asp Arg
        115                 120                 125
```

Gly Ala Ala Ala Ala Gly Tyr Ala Asp His Gly Cys Thr Gly Glu
130                 135                 140

Glu Ala Asn Ala Gly Ala Ala Ala Ala Gly Gln Lys Ile Lys Gly
145             150                 155                 160

Trp Tyr Glu Lys Tyr Gly Pro Gly Ser Gly Arg Gln Gly Ala Ala Ala
                165             170                 175

Ala Ala Gly Asp Tyr Ser Lys Tyr Phe Ser Ala Thr Glu Asp Ala Lys
            180             185                 190

Arg Gln Ser Gly Thr Thr Cys Gly Ala Ala Ala Ala Gly Ala Gly
        195                 200                 205

Gln Asn Glu Asn Ala Arg Ala Thr Ala Asp Asp Phe Arg Gly Lys Cys
210             215                 220

Glu Asn Gly Ala Ala Ala Ala Gly His Gln Ser Gly Glu Ala Asp
225                 230                 235                 240

Ile Asn Gly Ala His Arg Ala Met Asp Glu Gly Ala Ala Ala Ala
                245                 250                 255

Ala Gly Thr Ser Asp Gly Glu Met Gln Cys Glu Ala Ala Ser Glu Glu
        260                 265                 270

Gly Thr Gly Ala Ala Ala Ala Gly Lys Asn His Gln Glu Glu Met
        275                 280                 285

Lys Gly
    290

<210> SEQ ID NO 14
<211> LENGTH: 560
<212> TYPE: PRT
<213> ORGANISM: Artificial Sequence
<220> FEATURE:
<223> OTHER INFORMATION: PRT855

<400> SEQUENCE: 14

Met His His His His His Ser Ser Gly Ser Ser Glu Gly Ala
1               5                   10                  15

Phe Gln Gly Pro Ser Phe Arg Gly Ser Gly Ala Ser Arg Gly Ala Ala
                20                  25                  30

Ala Ala Ala Gly Ser Gln Ala Gly Thr Gly Arg Gly Thr Gly Arg
            35                  40                  45

Thr Gly Phe Arg Ala Gly Asn Gly Cys Ser Gly Ala Gly Ala Ala Ala
    50                  55                  60

Ala Ala Gly Ser Ser Phe Ser Gly Pro Gly Gly Ser Ala Ser Ser Lys
65                  70                  75                  80

Gly Ser Phe Ser His Gly Gly Ala Ala Ala Ala Gly Gly Ala Gly
                85                  90                  95

Ser Gly Gly Cys Thr Gly Phe Gly Glu Asn Glu His Gly Ala Ala Ala
                100                 105                 110

Ala Ala Gly Gly Asn Glu Lys Ala Thr Gly Gln Asn Ala Asn Asp Arg
            115                 120                 125

Gly Ala Ala Ala Ala Gly Tyr Ala Asp His Gly Cys Thr Gly Glu
        130                 135                 140

Glu Ala Asn Ala Gly Ala Ala Ala Ala Gly Gln Lys Ile Lys Gly
145             150                 155                 160

Trp Tyr Glu Lys Tyr Gly Pro Gly Ser Gly Arg Gln Gly Ala Ala Ala
                165             170                 175

Ala Ala Gly Asp Tyr Ser Lys Tyr Phe Ser Ala Thr Glu Asp Ala Lys
            180             185                 190

```
Arg Gln Ser Gly Thr Thr Cys Gly Ala Ala Ala Ala Gly Ala Gly
        195                 200                 205

Gln Asn Glu Asn Ala Arg Ala Thr Ala Asp Asp Phe Arg Gly Lys Cys
210                 215                 220

Glu Asn Gly Ala Ala Ala Ala Gly His Gln Ser Gly Glu Ala Asp
225                 230                 235                 240

Ile Asn Gly Ala His Arg Ala Met Asp Glu Gly Ala Ala Ala
                245                 250                 255

Ala Gly Thr Ser Asp Gly Glu Met Gln Cys Glu Ala Ala Ser Glu Glu
        260                 265                 270

Gly Thr Gly Ala Ala Ala Ala Gly Lys Asn His Gln Glu Glu Met
        275                 280                 285

Lys Gly Ser Phe Arg Gly Ser Gly Ala Ser Arg Gly Ala Ala Ala
    290                 295                 300

Ala Gly Ser Gln Ala Gly Thr Gly Arg Gly Thr Gly Arg Thr Gly
305                 310                 315                 320

Phe Arg Ala Gly Asn Gly Cys Ser Gly Ala Gly Ala Ala Ala
                325                 330                 335

Gly Ser Ser Phe Ser Gly Pro Gly Gly Ser Ala Ser Ser Lys Gly Ser
        340                 345                 350

Phe Ser His Gly Gly Ala Ala Ala Ala Gly Gly Ala Gly Ser Gly
        355                 360                 365

Gly Cys Thr Gly Phe Gly Glu Asn Glu His Gly Ala Ala Ala Ala
        370                 375                 380

Gly Gly Asn Glu Lys Ala Thr Gly Gln Asn Ala Asn Asp Arg Gly Ala
385                 390                 395                 400

Ala Ala Ala Gly Tyr Ala Asp His Gly Cys Thr Gly Glu Glu Ala
                405                 410                 415

Asn Ala Gly Ala Ala Ala Ala Gly Gln Lys Ile Lys Gly Trp Tyr
                420                 425                 430

Glu Lys Tyr Gly Pro Gly Ser Gly Arg Gln Gly Ala Ala Ala Ala
        435                 440                 445

Gly Asp Tyr Ser Lys Tyr Phe Ser Ala Thr Glu Asp Ala Lys Arg Gln
450                 455                 460

Ser Gly Thr Thr Cys Gly Ala Ala Ala Gly Ala Gly Gln Asn
465                 470                 475                 480

Glu Asn Ala Arg Ala Thr Ala Asp Asp Phe Arg Gly Lys Cys Glu Asn
                485                 490                 495

Gly Ala Ala Ala Ala Gly His Gln Ser Gly Glu Ala Asp Ile Asn
        500                 505                 510

Gly Ala His Arg Ala Met Asp Glu Gly Gly Ala Ala Ala Ala Gly
        515                 520                 525

Thr Ser Asp Gly Glu Met Gln Cys Glu Ala Ala Ser Glu Glu Gly Thr
        530                 535                 540

Gly Ala Ala Ala Ala Gly Lys Asn His Gln Glu Glu Met Lys Gly
545                 550                 555                 560

<210> SEQ ID NO 15
<211> LENGTH: 290
<212> TYPE: PRT
<213> ORGANISM: Artificial Sequence
<220> FEATURE:
<223> OTHER INFORMATION: PRT837

<400> SEQUENCE: 15
```

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
50                  55                  60

Ala Ala Ala Ala Gly Pro Gly Tyr Gly Pro Gly Gln Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Gly
        130                 135                 140

Pro Gly Ser Gly Gln Tyr Gly Gln Gly Pro Tyr Gly Ala Glu Ala Trp
145                 150                 155                 160

Phe Ser Glu Lys Ser Thr Ser Gly His Gln Gln Ile Ser Asp Asp Ala
                165                 170                 175

Gly Ala Ala Met Ala Ala Arg Asn Glu Ala Met Glu Gly Lys Arg Asn
            180                 185                 190

Ala Gln Thr Gly Glu Ile Glu Ala Gln Ser Gly Ala Ala Met Lys His
            195                 200                 205

Ser Tyr Glu Cys Ser Gly Ala Glu Thr Glu Ser Asn Tyr Cys His Gln
    210                 215                 220

Ala Gln Gln Ile Gln Glu Gln Ile Gly Ala Met Glu Asp Gln Ala Gln
225                 230                 235                 240

Gln Ile Arg Met Glu Thr Glu Gly Gln Lys Gly Glu His Glu Arg Ala
            245                 250                 255

Gly Asp Val Lys Ile Phe Ala Glu Lys Glu Ile Glu Met Tyr Cys Lys
            260                 265                 270

Gly Ile Asp Gly Glu Gly Arg Lys Ser Lys Ser Thr Cys Tyr Lys Ser
        275                 280                 285

Glu Gly
    290

<210> SEQ ID NO 16
<211> LENGTH: 290
<212> TYPE: PRT
<213> ORGANISM: Artificial Sequence
<220> FEATURE:
<223> OTHER INFORMATION: PRT838

<400> SEQUENCE: 16

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
50                  55                  60

```
Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
    115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Ala Glu Ala Trp
145                 150                 155                 160

Phe Ser Glu Lys Ser Thr Ser Gly His Gln Gln Ile Ser Asp Asp Ala
                165                 170                 175

Gly Ala Ala Met Ala Ala Arg Asn Glu Ala Met Glu Gly Lys Arg Asn
                180                 185                 190

Ala Gln Thr Gly Glu Ile Glu Ala Gln Ser Gly Ala Ala Met Lys His
            195                 200                 205

Ser Tyr Glu Cys Ser Gly Ala Glu Thr Glu Ser Asn Tyr Cys His Gln
    210                 215                 220

Ala Gln Gln Ile Gln Glu Gln Ile Gly Ala Met Glu Asp Gln Ala Gln
225                 230                 235                 240

Gln Ile Arg Met Glu Thr Glu Gly Gln Lys Gly Glu His Glu Arg Ala
                245                 250                 255

Gly Asp Ala Lys Ile Phe Ala Glu Lys Glu Ile Glu Met Tyr Cys Lys
            260                 265                 270

Gly Ile Asp Gly Glu Gly Arg Lys Ser Lys Ser Thr Cys Tyr Lys Ser
            275                 280                 285

Glu Gly
    290

<210> SEQ ID NO 17
<211> LENGTH: 12
<212> TYPE: PRT
<213> ORGANISM: Artificial Sequence
<220> FEATURE:
<223> OTHER INFORMATION: HisTag

<400> SEQUENCE: 17

Met His His His His His His Ser Ser Gly Ser Ser
1               5                   10
```